United States Patent
Vidyasagar et al.

(10) Patent No.: US 12,357,600 B2
(45) Date of Patent: *Jul. 15, 2025

(54) FORMULATIONS FOR PROMOTING HYDRATION AND METHODS OF USE THEREOF

(71) Applicants: UNIVERSITY OF FLORIDA RESEARCH FOUNDATION, INCORPORATED, Gainsville, FL (US); AMILYFE, LLC, Norwood, MA (US)

(72) Inventors: Sadasivan Vidyasagar, Gainsville, FL (US); Astrid Grosche, Gainsville, FL (US); Xiaodong Xu, Gainsville, FL (US); Shanshan Lin, Gainsville, FL (US); Samuel Cheuvront, Norwood, MA (US); Robert Kenefick, Norwood, MA (US); Stephen Gatto, Norwood, MA (US)

(73) Assignees: UNIVERSITY OF FLORIDA RESEARCH FOUNDATION, INCORPORATED, Gainsville, FL (US); AMILYFE, LLC., Norwood, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,903

(22) Filed: Dec. 30, 2022

(65) Prior Publication Data
US 2023/0149335 A1 May 18, 2023

Related U.S. Application Data

(63) Continuation of application No. PCT/US2021/040090, filed on Jul. 1, 2021.
(Continued)

(51) Int. Cl.
*A61K 31/198* (2006.01)
*A61K 45/06* (2006.01)
*A61P 1/00* (2006.01)

(52) U.S. Cl.
CPC ............ *A61K 31/198* (2013.01); *A61K 45/06* (2013.01); *A61P 1/00* (2018.01)

(58) Field of Classification Search
CPC .......... A61K 31/198; A61K 45/06; A61P 1/00
See application file for complete search history.

(56) References Cited

U.S. PATENT DOCUMENTS

| 8,993,522 B2 | 3/2015 | Vidyasager et al. |
| 2014/0377374 A1 | 12/2014 | Vidyasager et al. |
| 2019/0046504 A1* | 2/2019 | Vidyasagar ............ A61K 47/22 |

FOREIGN PATENT DOCUMENTS

| WO | 2010017403 A9 | 2/2010 |
| WO | 2018067717 A1 | 4/2018 |
| WO | 2019070753 A1 | 4/2019 |

OTHER PUBLICATIONS

Yin, L., et al (2014) An amino acid mixture mitigates radiation-induced gastrointestinal toxicity Health physics 106(6); 734-744 (Year : 2014).*

(Continued)

*Primary Examiner* — Scarlett Y Goon
*Assistant Examiner* — Audrey L Buttice
(74) *Attorney, Agent, or Firm* — Greenberg Traurig, LLP

(57) ABSTRACT

Formulations comprising particular free amino acids useful for promoting hydration and/or intestinal barrier function in a subject in need thereof are described herein. Such formulations and methods using same are useful for promoting hydration and/or intestinal barrier function in a subject in need thereof. Such subjects may be healthy, but in need of a formulation that promotes rapid hydration (e.g., within 15-90 minutes post-administration) or promotes intestinal (Continued)

barrier function; or such subjects may be afflicted by a disorder or disease associated with dehydration or impaired intestinal barrier function, respectively. Use of amino acid formulations described herein for promoting hydration and/or intestinal barrier function in a subject in need thereof, for the treatment of disorders or diseases associated dehydration and/or impaired intestinal barrier function, and in the preparation of a medicament for the treatment of disorders or diseases associated with dehydration and/or impaired intestinal barrier function are encompassed herein.

13 Claims, 6 Drawing Sheets

Related U.S. Application Data

(60) Provisional application No. 63/047,300, filed on Jul. 2, 2020.

(56) References Cited

OTHER PUBLICATIONS

International Search Report and Written Opinion to corresponding International Application No. PCT/US2021/040090, 14 pages, mailed Oct. 13, 2021.

\* cited by examiner

FORMULATIONS FOR PROMOTING HYDRATION AND METHODS OF USE THEREOF

RELATED APPLICATIONS

This application claims priority of U.S. Provisional Application No. 63/047,300 filed Jul. 2, 2020, the entirety of which is incorporated herein by reference for all purposes.

FIELD OF THE INVENTION

Amino acid formulations useful for promoting hydration and/or intestinal barrier function in a subject in need thereof are described herein. Formulations and methods described herein are useful for promoting hydration and/or intestinal barrier function in a subject in need thereof. In some embodiments, such subjects are healthy, but are in need of or want a formulation that promotes rapid hydration (e.g., within 15-90 minutes post-administration) and/or promotes intestinal barrier function. In some embodiments, such subjects are afflicted by a disorder or disease associated with dehydration and/or impaired intestinal barrier function. Use of amino acid formulations described herein for promoting hydration and/or intestinal barrier function in a subject in need thereof, for the treatment of disorders or diseases associated dehydration and/or impaired intestinal barrier function, and in the preparation of a medicament for the treatment of disorders or diseases associated with dehydration and/or impaired intestinal barrier function are also encompassed herein.

BACKGROUND OF THE INVENTION

Dehydration occurs in a subject when water loss exceeds water intake. Dehydration can range from mild forms of dehydration, which can be addressed by increasing fluid intake, to severe forms of dehydration, which can require medical attention. Dehydration can result from a variety of reasons, including, without limitation: excessive sweating associated with physical exertion, prolonged exposure to high temperatures (e.g., temperatures ≥37° C.) and/or low humidity (e.g., such as that typical of a desert climate), and diseases or disorders associated with vomiting and/or diarrhea.

Rapid gastric emptying and intestinal absorption of ingested fluids is essential for quickly replacing sweat losses incurred during exercise-heat stress. Failure to replace sweat losses leads to dehydration, which increases physiological strain and impairs endurance performance—particularly in the heat. The rate by which ingested fluids are made available to replace sweat losses is dependent on the speed at which fluids empty from the stomach (gastric emptying rate) and the rate of absorption at the site of the intestine.

SUMMARY

Covered embodiments are defined by the claims, not this summary. This summary is a high-level overview of various aspects and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

In some embodiments, a formulation for use in promoting hydration in a subject in need thereof is presented, wherein the formulation comprises: a therapeutically effective combination of free amino acids, wherein the free amino acids consist essentially of a therapeutically effective amount of free amino acids of tyrosine, isoleucine, threonine, valine, serine, and aspartic acid; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject.

In some embodiments, a formulation for use in promoting intestinal barrier function in a subject in need thereof is presented, wherein the formulation comprises: a therapeutically effective combination of free amino acids, wherein the free amino acids consist essentially of a therapeutically effective amount of free amino acids of tyrosine, isoleucine, threonine, valine, serine, and aspartic acid; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject.

In some embodiments of the formulation or use, a total weight percent of aspartic acid and serine is greater than a total weight percent of valine, isoleucine, threonine, and tyrosine.

In some embodiments of the formulation or use, a molar ratio of aspartic acid/serine ranges from 2.8 aspartic acid/1 serine to 0.9 aspartic acid/1 serine.

In some embodiments of the formulation or use, the formulation does not comprise free amino acids of lysine, glycine, or tryptophan, or any combination thereof; or when present, each of the free amino acids of lysine, glycine, or tryptophan, or any combination thereof is present in a negligible amount. In some embodiments thereof, a negligible amount of lysine is less than 1 mM, a negligible amount of glycine is less than 0.5 mM, and/or a negligible amount of glycine is less than 0.5 mM.

In some embodiments of the formulation or use, the therapeutically effective combination of free amino acids consists of free amino acids of tyrosine, isoleucine, threonine, valine, serine, and aspartic acid.

In some embodiments of the formulation or use, a concentration of aspartic acid ranges from 14 mM to 30 mM. In some embodiments thereof, the formulation is in solution.

In some embodiments of the formulation or use, the concentration of aspartic acid ranges from 15 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM.

In some embodiments of the formulation or use, the molar ratio of aspartic acid/serine ranges from 2.8 aspartic acid/1 serine to 1 aspartic acid/1 serine; the molar ratio of aspartic acid/serine ranges from 2.7 aspartic acid/1 serine to 1 aspartic acid/1 serine; the molar ratio of aspartic acid/serine ranges from 2.6 aspartic acid/1 serine to 1 aspartic acid/1 serine; the molar ratio of aspartic acid/serine ranges from 2.5 aspartic acid/1 serine to 1 aspartic acid/1 serine; the molar ratio of aspartic acid/serine ranges from 2.4 aspartic acid/1 serine to 1 aspartic acid/1 serine; the molar ratio of aspartic acid/serine ranges from 2.3 aspartic acid/1 serine to 1 aspartic acid/1 serine; the molar ratio of aspartic acid/serine ranges from 2.2 aspartic acid/1 serine to 1 aspartic acid/1 serine; the molar ratio of aspartic acid/serine ranges from 2.1 aspartic acid/1 serine to 1 aspartic acid/1 serine; the molar ratio of aspartic acid/serine ranges from 2.0 aspartic acid/1 serine to 1 aspartic acid/1 serine; the molar ratio of aspartic acid/serine ranges from 1.9 aspartic acid/1 serine to 1 aspartic acid/1 serine; the molar ratio of aspartic acid/serine ranges from 1.8 aspartic acid/1 serine to 1 aspartic acid/1 serine; the molar ratio of aspartic acid/serine ranges from 1.7 aspartic acid/1 serine to 1 aspartic acid/1 serine; the molar ratio of aspartic acid/serine ranges from 1.6 aspartic acid/1 serine to 1 aspartic acid/1 serine; the molar ratio of aspartic acid/serine ranges from 1.5 aspartic acid/1 serine to 1 aspartic acid/1 serine; the molar ratio of aspartic acid/serine ranges from 1.4 aspartic acid/1 serine to 1 aspartic acid/1 serine; the molar ratio of aspartic acid/serine ranges from 1.3 aspartic acid/1 serine to 1 aspartic acid/1 serine; the molar ratio of aspartic acid/serine ranges from 1.2 aspartic acid/1 serine to 1 aspartic acid/1 serine; the molar ratio of aspartic acid/serine ranges from 1.1 aspartic acid/1 serine to 1 aspartic acid/1 serine; the molar ratio is about 2.8 aspartic acid/1 serine; the molar ratio is about 0.9 aspartic acid/1 serine; the molar ratio is about 1.8 aspartic acid/1 serine; or the molar ratio is about 1.2 aspartic acid/1 serine.

In some embodiments of the formulation or use, the molar ratio of aspartic acid/valine ranges from 3.8 aspartic acid/1 valine to 1.4 aspartic acid/1 valine; the molar ratio of aspartic acid/valine ranges from 3.8 aspartic acid/1 valine to 1.5 aspartic acid/1 valine; the molar ratio of aspartic acid/valine ranges from 3.8 aspartic acid/1 valine to 1.6 aspartic acid/1 valine; the molar ratio of aspartic acid/valine ranges from 3.8 aspartic acid/1 valine to 1.7 aspartic acid/1 valine; the molar ratio of aspartic acid/valine ranges from 3.8 aspartic acid/1 valine to 1.8 aspartic acid/1 valine; the molar ratio of aspartic acid/valine ranges from 3.6 aspartic acid/1 valine to 1.4 aspartic acid/1 valine; the molar ratio of aspartic acid/valine ranges from 3.6 aspartic acid/1 valine to 1.5 aspartic acid/1 valine; the molar ratio of aspartic acid/valine ranges from 3.6 aspartic acid/1 valine to 1.6 aspartic acid/1 valine; the molar ratio of aspartic acid/valine ranges from 3.6 aspartic acid/1 valine to 1.7 aspartic acid/1 valine; the molar ratio of aspartic acid/valine ranges from 3.6 aspartic acid/1 valine to 1.8 aspartic acid/1 valine; the molar ratio of aspartic acid/valine ranges from 3.5 aspartic acid/1 valine to 1.8 aspartic acid/1 valine; the molar ratio of aspartic acid/valine ranges from 3.2 aspartic acid/1 valine to 1.9 aspartic acid/1 valine; the molar ratio of aspartic acid/valine ranges from 3.2 aspartic acid/1 valine to 2.0 aspartic acid/1 valine; the molar ratio of aspartic acid/valine ranges from 2.5 aspartic acid/1 valine to 2.0 aspartic acid/1 valine; the molar ratio of aspartic acid/valine ranges from 2.2 aspartic acid/1 valine to 2.0 aspartic acid/1 valine; the molar ratio of aspartic acid/valine ranges from 2.1 aspartic acid/1 valine to 2.0 aspartic acid/1 valine; the molar ratio of aspartic acid/valine is about 3.8 aspartic acid/1 valine; the molar ratio of aspartic acid/valine is about 1.4 aspartic acid/1 valine; the molar ratio of aspartic acid/valine is about 3.2 aspartic acid/1 valine; or the molar ratio of aspartic acid/valine is about 2 aspartic acid/1 valine.

In some embodiments of the formulation or use, the molar ratio of aspartic acid/isoleucine ranges from 5.5 aspartic acid/1 isoleucine to 1.5 aspartic acid/1 isoleucine; the molar ratio of aspartic acid/isoleucine ranges from 5.5 aspartic acid/1 isoleucine to 1.6 aspartic acid/1 isoleucine; the molar ratio of aspartic acid/isoleucine ranges from 5.5 aspartic acid/1 isoleucine to 1.7 aspartic acid/1 isoleucine; the molar ratio of aspartic acid/isoleucine ranges from 5.5 aspartic acid/1 isoleucine to 1.8 aspartic acid/1 isoleucine; the molar ratio of aspartic acid/isoleucine ranges from 5.5 aspartic acid/1 isoleucine to 1.9 aspartic acid/1 isoleucine; the molar ratio of aspartic acid/isoleucine ranges from 5.5 aspartic acid/1 isoleucine to 2.0 aspartic acid/1 isoleucine; the molar ratio of aspartic acid/isoleucine ranges from 5.0 aspartic acid/1 isoleucine to 1.5 aspartic acid/1 isoleucine; the molar ratio of aspartic acid/isoleucine ranges from 5.0 aspartic acid/1 isoleucine to 1.6 aspartic acid/1 isoleucine; the molar ratio of aspartic acid/isoleucine ranges from 5.0 aspartic acid/1 isoleucine to 1.7 aspartic acid/1 isoleucine; the molar ratio of aspartic acid/isoleucine ranges from 5.0 aspartic acid/1 isoleucine to 1.8 aspartic acid/1 isoleucine; the molar ratio of aspartic acid/isoleucine ranges from 5.0 aspartic acid/1 isoleucine to 1.9 aspartic acid/1 isoleucine; the molar ratio of aspartic acid/isoleucine ranges from 5.0 aspartic acid/1 isoleucine to 2.0 aspartic acid/1 isoleucine; the molar ratio of aspartic acid/isoleucine ranges from 4.9 aspartic acid/1 isoleucine to 2.5 aspartic acid/1 isoleucine; the molar ratio of aspartic acid/isoleucine ranges from 4.8 aspartic acid/1 isoleucine to 2.5 aspartic acid/1 isoleucine; the molar ratio of aspartic acid/isoleucine ranges from 4.7 aspartic acid/1 isoleucine to 2.5 aspartic acid/1 isoleucine; the molar ratio of aspartic acid/isoleucine ranges from 4.6 aspartic acid/1 isoleucine to 2.5 aspartic acid/1 isoleucine; the molar ratio of aspartic acid/isoleucine ranges from 4.5 aspartic acid/1 isoleucine to 2.5 aspartic acid/1 isoleucine; the molar ratio of aspartic acid/isoleucine ranges from 4.4 aspartic acid/1 isoleucine to 2.5 aspartic acid/1 isoleucine; the molar ratio of aspartic acid/isoleucine ranges from 4.4 aspartic acid/1 isoleucine to 2.6 aspartic acid/1 isoleucine; the molar ratio of aspartic acid/isoleucine ranges from 4.4 aspartic acid/1 isoleucine to 2.7 aspartic acid/1 isoleucine; the molar ratio of aspartic acid/isoleucine ranges from 4.4 aspartic acid/1 isoleucine to 2.8 aspartic acid/1 isoleucine; the molar ratio of aspartic acid/isoleucine is about 5.5 aspartic acid/1 isoleucine; the molar ratio of aspartic acid/isoleucine is about 1.5 aspartic acid/1 isoleucine; the molar ratio of aspartic acid/isoleucine is about 4.4 aspartic acid/1 isoleucine; or the molar ratio of aspartic acid/isoleucine is about 2.8 aspartic acid/1 isoleucine.

In some embodiments of the formulation or use, the molar ratio of aspartic acid/threonine ranges from 5.5 aspartic acid/1 threonine to 1.7 aspartic acid/1 threonine; the molar ratio of aspartic acid/threonine ranges from 5.5 aspartic acid/1 threonine to 1.8 aspartic acid/1 threonine; the molar ratio of aspartic acid/threonine ranges from 5.5 aspartic acid/1 threonine to 1.9 aspartic acid/1 threonine; the molar ratio of aspartic acid/threonine ranges from 5.5 aspartic acid/1 threonine to 2.0 aspartic acid/1 threonine; the molar ratio of aspartic acid/threonine ranges from 5.0 aspartic acid/1 threonine to 1.7 aspartic acid/1 threonine; the molar ratio of aspartic acid/threonine ranges from 5.0 aspartic acid/1 threonine to 1.8 aspartic acid/1 threonine; the molar ratio of aspartic acid/threonine ranges from 5.0 aspartic acid/1 threonine to 1.9 aspartic acid/1 threonine; the molar ratio of aspartic acid/threonine ranges from 5.0 aspartic acid/1 threonine to 2.0 aspartic acid/1 threonine; the molar ratio of aspartic acid/threonine ranges from 4.9 aspartic acid/1 threonine to 2.5 aspartic acid/1 threonine; the molar ratio of aspartic acid/threonine ranges from 4.8 aspartic acid/1 threonine to 2.5 aspartic acid/1 threonine; the molar ratio of aspartic acid/threonine ranges from 4.7 aspartic acid/1 threonine to 2.5 aspartic acid/1 threonine; the molar ratio of aspartic acid/threonine ranges from 4.6 aspartic acid/1 threonine to 2.5 aspartic acid/1 threonine; the molar ratio of aspartic acid/threonine ranges from 4.5 aspartic acid/1 threonine to 2.5 aspartic acid/1 threonine; the molar ratio of aspartic acid/threonine ranges from 4.4 aspartic acid/1 threonine to 2.5 aspartic acid/1 threonine; the molar ratio of aspartic acid/threonine ranges from 4.4 aspartic acid/1 threonine to 2.6 aspartic acid/1 threonine; the molar ratio of aspartic acid/threonine ranges from 4.4 aspartic acid/1 threonine to 2.7 aspartic acid/1 threonine; the molar ratio of aspartic acid/threonine ranges from 4.4 aspartic acid/1 threonine to 2.8 aspartic acid/1 threonine; the molar ratio of aspartic acid/threonine is about 5.5 aspartic acid/1 threonine; the molar ratio of aspartic acid/threonine is about 1.7 aspartic acid/1 threonine; the molar ratio of aspartic acid/threonine is about 4.4 aspartic acid/1 threonine; or the molar ratio of aspartic acid/threonine is about 2.8 aspartic acid/1 threonine.

In some embodiments of the formulation or use, the molar ratio of aspartic acid/tyrosine ranges from 40.0 aspartic acid/1 tyrosine to 9.0 aspartic acid/1 tyrosine; the molar ratio of aspartic acid/tyrosine ranges from 36.0 aspartic acid/1 tyrosine to 10.0 aspartic acid/1 tyrosine; the molar ratio of aspartic acid/tyrosine ranges from 36.0 aspartic acid/1 tyrosine to 15.0 aspartic acid/1 tyrosine; the molar ratio of aspartic acid/tyrosine ranges from 36.0 aspartic acid/1 tyrosine to 20.0 aspartic acid/1 tyrosine; the molar ratio of aspartic acid/tyrosine ranges from 24.0 aspartic acid/1 tyrosine to 10.0 aspartic acid/1 tyrosine; the molar ratio of aspartic acid/tyrosine ranges from 24.0 aspartic acid/1 tyrosine to 15.0 aspartic acid/1 tyrosine; the molar ratio of aspartic acid/tyrosine ranges from 24.0 aspartic acid/1 tyrosine to 20.0 aspartic acid/1 tyrosine; the molar ratio of aspartic acid/tyrosine is about 35.8 aspartic acid/1 tyrosine; the molar ratio of aspartic acid/tyrosine is about 23.8 aspartic acid/1 tyrosine; the molar ratio of aspartic acid/tyrosine is about 23.0 aspartic acid/1 tyrosine; the molar ratio of aspartic acid/tyrosine is about 17.5 aspartic acid/1 tyrosine; the molar ratio of aspartic acid/tyrosine is about 15.3 aspartic acid/1 tyrosine; or the molar ratio of aspartic acid/tyrosine is about 11.7 aspartic acid/1 tyrosine.

In some embodiments of the formulation or use, the formulation further comprises at least one salt.

In some embodiments of the formulation or use, at least one of the free amino acids or each of the free amino acids is an L-amino acid.

In some embodiments of the formulation or use, the promoted fluid absorption reflects an increased rate of fluid absorption in the subject, wherein the increased rate is determined relative to the same formulation without free amino acids. In some embodiments thereof, the increased rate determined relative to the same formulation without free amino acids comprises a relative increase of at least 15%.

In some embodiments of the formulation or use, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof.

In some embodiments of the formulation or use, the formulation is formulated for administration by an enteral route. In some embodiments thereof, the formulation is formulated for oral administration.

In some embodiments of the formulation or use, a beverage comprises the formulation. In some embodiments of the formulation or use, the formulation is used in the form of a beverage.

In some embodiments of the formulation or use, the subject is a mammal. In some embodiments thereof, the mammal is a human, cat, dog, pig, horse, cow, sheep, bison, or goat. In some embodiments of the formulation or use, the subject is a bird or a reptile. In some embodiments thereof, the bird is a chicken, turkey, duck, goose, quail, pigeon, peacock, parrot (e.g., a conure), cockatiel, cockatoo, or other domesticated or household pet bird species.

In some embodiments of the formulation or use, the formulation is for use in promoting hydration in a healthy subject.

In some embodiments of the formulation or use, the formulation is for use in the treatment of a disease or disorder associated with dehydration in a subject in need thereof.

In some embodiments of the formulation or use, the formulation is used in the preparation of a medicament for promoting hydration in a healthy subject or for treating a disease or disorder associated with dehydration in a subject in need thereof.

In some embodiments of the formulation or use, the formulation is used in a method for promoting hydration in a healthy subject or for treating a disease or disorder associated with dehydration in a subject in need thereof.

In some embodiments of the formulation, use, medicament, or method, the disease or disorder associated with dehydration comprises at least one of a fever, edema, incontinence, or renal failure, or any combination thereof.

In some embodiments, a formulation for use in promoting hydration in a subject in need thereof is presented, wherein the formulation comprises: a therapeutically effective combination of free amino acids, wherein the therapeutically effective combination of free amino acids consists essentially of: a therapeutically effective amount of free amino acids of aspartic acid and serine; a therapeutically effective amount of at least one of free amino acids of valine, isoleucine, threonine, or tyrosine, or any combination thereof; and water; wherein a molar ratio of aspartic acid/serine ranges from 2.8 aspartic acid/1 serine to 0.9 aspartic acid/1 serine; and wherein the therapeutically effective combination of free amino acids is sufficient to promote hydration in the subject. In some embodiments of the formulation or use, the concentration of aspartic acid ranges from 14 mM to 30 mM. In some embodiments thereof, the formulation is in solution. In some embodiments of the formulation or use, the therapeutically effective combination of free amino acids consists essentially of: a therapeutically effective amount of free amino acids of aspartic acid, serine, and valine; and a therapeutically effective amount of at least one of free amino acids of isoleucine, threonine, or tyrosine, or any combination thereof. In some embodiments of the formulation or use, a total weight percent of aspartic acid and serine is greater than a total weight percent of valine, isoleucine, threonine, and tyrosine.

In some embodiments, a formulation for use in promoting hydration in a subject in need thereof is presented, wherein the formulation comprises: a therapeutically effective combination of free amino acids, wherein the therapeutically effective combination of free amino acids consists essentially of: a therapeutically effective amount of free amino acids of aspartic acid and valine; and a therapeutically effective amount of at least one of free amino acids of serine, isoleucine, threonine, or tyrosine, or any combination thereof; and water; wherein a molar ratio of aspartic acid/valine ranges from 3.8 aspartic acid/1 valine to 1.4 aspartic acid/1 valine; and wherein the therapeutically effective combination of free amino acids is sufficient to promote hydration in the subject. In some embodiments of the formulation or use, the concentration of aspartic acid ranges from 14 mM to 30 mM. In some embodiments thereof, the formulation is in solution. In some embodiments of the formulation or use, the concentration of aspartic acid ranges from 15 mM to 20 mM; wherein the concentration of aspartic acid ranges from 17 mM to 20 mM; wherein the concentration of aspartic acid ranges from 18 mM to 19 mM; wherein the concentration of aspartic acid ranges from 20 mM to 30 mM; wherein the concentration of aspartic acid ranges from 25 mM to 30 mM; wherein the concentration of aspartic acid ranges from 27 mM to 30 mM; or wherein the concentration of aspartic acid ranges from 28 mM to 29 mM. In some embodiments of the formulation or use, the formulation further comprises at least one salt.

In some embodiments, a therapeutic formulation is presented comprising: a therapeutically effective combination of free amino acids, wherein the free amino acids consist essentially of a therapeutically effective amount of free amino acids of tyrosine, isoleucine, threonine, valine, serine, and aspartic acid; wherein a total weight percent of free amino acids of aspartic acid ranges from 30% to 55% of a total weight of the combination of free amino acids; and optionally, at least one pharmaceutically acceptable carrier, buffer, electrolyte, adjuvant, excipient, or water, or any combination thereof. In some embodiments of the formulation, a total weight percent of aspartic acid and serine is greater than a total weight percent of valine, isoleucine, threonine, and tyrosine. In some embodiments of the formulation, a molar ratio of aspartic acid/serine ranges from 2.8 aspartic acid/1 serine to 0.9 aspartic acid/1 serine. In some embodiments of the formulation, the concentration of aspartic acid ranges from 14 mM to 30 mM. In some embodiments thereof, the formulation is in solution. In some embodiments of the formulation, the formulation does not comprise free amino acids of lysine, glycine, or tryptophan, or any combination thereof; or when present, each of the free amino acids of lysine, glycine, or tryptophan, or any combination thereof is present in a negligible amount. In some embodiments thereof, a negligible amount of lysine is less than 1 mM, a negligible amount of glycine is less than 0.5 mM, and/or a negligible amount of glycine is less than 0.5 mM. In some embodiments of the formulation, the combination of free amino acids consists of free amino acids of tyrosine, isoleucine, threonine, valine, serine, and aspartic acid. In some embodiments of the formulation, the formulation further comprises at least one salt.

In some embodiments, an amino acid formulation described herein is used to promote hydration in a healthy subject. Such subjects may, for example, be engaged in physical activities that reduce hydration levels. Such healthy subjects may be of any age. With respect to humans, for example, a healthy subject may be a baby, child, adult, or an older adult (e.g., 65 years or more old).

In some embodiments, an amino acid formulation described herein is used for the treatment of a disease or disorder associated with dehydration in a subject in need thereof. Exemplary such diseases or disorders associated with dehydration comprise: a fever; edema, which results in increased loss of fluids into abdominal cavities or organs (such as that observed with, for example, peritonitis); and incontinence (particularly in humans equal to or over the age of 70 years), which results in increased loss of fluids via increased urine production; and/or renal failure.

In some embodiments, an amino acid formulation described herein is used in the preparation of a medicament for treating a disease or disorder associated with dehydration in a subject in need thereof. Exemplary such diseases or disorders associated with dehydration comprise: a fever; edema, which results in increased loss of fluids into abdominal cavities or organs (such as that observed with, for example, peritonitis); and incontinence (particularly in humans equal to or over the age of 70 years), which results in increased loss of fluids via increased urine production; and/or renal failure.

In some embodiments, an amino acid formulation described herein is used in a method for treating a disease or disorder associated with dehydration in a subject in need thereof. Exemplary such diseases or disorders associated with dehydration comprise: a fever; edema, which results in increased loss of fluids into abdominal cavities or organs (such as that observed with, for example, peritonitis); and incontinence (particularly in humans equal to or over the age of 70 years), which results in increased loss of fluids via increased urine production; and/or renal failure.

In some embodiments, the subject has been diagnosed with a disease or disorder associated with dehydration. In some embodiments, the human or other mammal is an elderly subject (e.g., a human equal to or over the age of 70 years). In some embodiments, an elderly subject may exhibit decreased fluid intake relative to a recommended intake suggested by a medical practitioner attending to the elderly subject or standards set by the medical establishment. In some embodiments, the subject has been diagnosed with a disease or disorder associated with dehydration, including without limitation: a fever; edema, which results in increased loss of fluids into abdominal cavities or organs (such as that observed with, for example, peritonitis); and incontinence (particularly in humans equal to or over the age of 70 years), which results in increased loss of fluids via increased urine production; and/or renal failure.

In some embodiments, a concentration of each of the free amino acids present in the formulation ranges from 0.1 mM to 30 mM. In some embodiments, a concentration of each of free amino acids of aspartic acid, serine, valine, isoleucine, and threonine present in the formulation ranges from 5 mM to 30 mM. In some embodiments, a concentration of each of free amino acids of aspartic acid, serine, and valine present in the formulation ranges from 8 mM to 30 mM. In some embodiments, a concentration of each of free amino acids of aspartic acid and serine present in the formulation ranges from 10 mM to 30 mM.

In some embodiments, the pH ranges from 2.0 to 8.0, 2.5 to 8.0, 3.0 to 8.0, 3.5 to 8.0, 4.0 to 8.0, 4.5 to 8.0, 5.0 to 8.0, 5.5 to 8.0, 6.0 to 8.0, 6.5 to 8.0, 7.0 to 8.0, 7.5 to 8.0, 2.0 to 3.0, 2.5 to 4.0; 3.0 to 4.0; 3.3 to 3.8, or is about 2.5, 2.6, 2.9, 3.4, or 3.8.

All combinations of separately described embodiments are envisaged.

BRIEF DESCRIPTION OF THE DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

DETAILED DESCRIPTION

Figure 1:
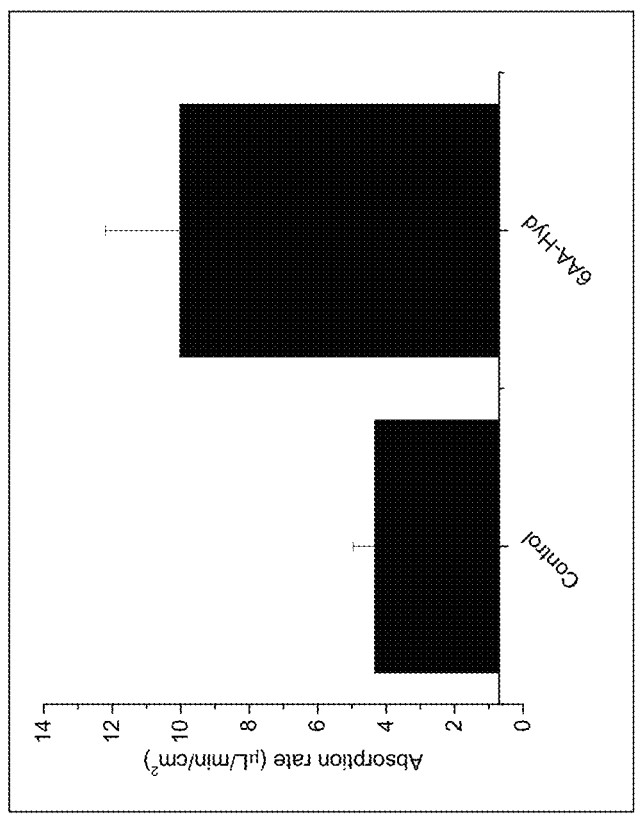
FIG. 1: Absorption rate as determined using a single-pass intestinal perfusion assay in rats at 15-90 minutes incubation time. Control (Ringer's saline with 17 mM Na); 6AA-Hydration ("6AA-Hyd"; Ringer's saline with 17 mM Na with tyrosine, isoleucine, threonine, valine, serine, and aspartic acid). The difference observed between Control vs. 6AA-Hyd is statistically significant as reflected by $P<0.05$.

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Amino acid formulations useful for promoting hydration in a subject in need thereof are described herein. Formulations and methods described herein are useful for promoting hydration in a subject in need thereof. In some embodiments, such subjects are healthy, but are in need of or want a formulation that promotes rapid hydration (e.g., within 15-90 minutes post-administration). In some embodiments, such subjects are afflicted by a disorder or disease associated with dehydration. Use of amino acid formulations described herein for promoting hydration in a subject in need thereof, for the treatment of disorders or diseases associated with dehydration, and in the preparation of a medicament for the treatment of disorders or diseases associated with dehydration are also encompassed herein.

Amino acid formulations useful for promoting intestinal barrier function in a subject in need thereof are described herein. Formulations and methods described herein are useful for promoting intestinal barrier function in a subject in need thereof. In some embodiments, such subjects are healthy, but are in need of or want a formulation that promotes intestinal barrier function. In some embodiments, such subjects are afflicted by a disorder or disease associated with impaired intestinal barrier function. Use of amino acid formulations described herein for promoting intestinal barrier function in a subject in need thereof, for the treatment of disorders or diseases associated with impaired intestinal barrier function, and in the preparation of a medicament for the treatment of disorders or diseases associated with impaired intestinal barrier function are also encompassed herein.

Barrier function is associated at least in part with tight junction integrity. Improvement in tight junction integrity is associated with reduced measurements of intestinal permeability, decreases in claudin-2 protein expression, and increases in occludin and e-cadherin proteins. Barrier restoration of damaged epithelia of the unrestricted flux pathway is also demonstrable by improvements in epithelial cells lining the villi and crypts, improvements in crypt and villus morphology, and LGR5+ stem cell proliferation. Improved barrier function reduces gut endotoxin, or leakage of other antigenic substances into the systemic compartment, thereby decreasing or preventing systemic inflammation.

Also encompassed herein is a method for promoting hydration in a subject in need thereof, the method comprising: orally administering to the subject an amino acid formulation described herein in an effective amount sufficient to promote fluid absorption in the subject in need thereof. In some embodiments, the amino acid formulation is administered in the form of a beverage comprising the amino acid formulation and optionally, flavorings. In some embodiments, such subjects are healthy, but are in need of or want a formulation that promotes rapid hydration (e.g., within 15-90 minutes post-administration). In some embodiments, such subjects are afflicted by a disorder or disease associated with dehydration.

Also encompassed herein is a method for promoting intestinal barrier function in a subject in need thereof, the method comprising: orally administering to the subject an amino acid formulation described herein in an effective amount sufficient to maintain or promote intestinal barrier integrity in the subject in need thereof. In some embodiments, the amino acid formulation is administered in the form of a beverage comprising the amino acid formulation and optionally, flavorings. In some embodiments, such subjects are healthy, but are in need of or want a formulation that promotes rapid hydration (e.g., within 15-90 minutes post-administration). In some embodiments, such subjects are afflicted by a disorder or disease associated with dehydration.

In some embodiments, "6AA-Hyd" is a formulation for use in promoting hydration and/or intestinal barrier function in a subject in need thereof, wherein the formulation comprises: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid, wherein a concentration of aspartic acid ranges from 14 mM to 30 mM; water; and optionally, at least one pharmaceutically acceptable carrier, buffer, electrolyte, adjuvant, excipient, or any combination thereof; wherein the therapeutically effective combination of free amino acids is sufficient to promote hydration or intestinal barrier integrity in the subject. In embodiments thereof, a molar ratio of aspartic acid/serine ranges from 2.8 aspartic acid/1 serine to 0.9 aspartic acid/1 serine. In embodiments thereof, a total weight percent of aspartic acid and serine is greater than a total weight percent of valine, isoleucine, threonine, and tyrosine. In embodiments thereof, the formulation does not comprise free amino acids of lysine, glycine, or tryptophan, or any combination thereof; or when present, each of the free amino acids of lysine, glycine, or tryptophan, or any combination thereof is present in a negligible amount. In embodiments thereof, the therapeutically effective combination of free amino acids consists of free amino acids of tyrosine, isoleucine, threonine, valine, serine, and aspartic acid. In embodiments thereof, the concentration of aspartic acid ranges from 15 mM to 20 mM; wherein the concentration of aspartic acid ranges from 17 mM to 20 mM; wherein the concentration of aspartic acid ranges from 18 mM to 19 mM; wherein the concentration of aspartic acid ranges from 20 mM to 30 mM; wherein the concentration of aspartic acid ranges from 25 mM to 30 mM; wherein the concentration of aspartic acid ranges from 27 mM to 30 mM; or wherein the concentration of aspartic acid ranges from 28 mM to 29 mM. In embodiments thereof, a molar ratio of aspartic acid/serine ranges from 2.8 aspartic acid/1 serine to 0.9 aspartic acid/1 serine; a molar ratio of aspartic acid/valine ranges from 3.8 aspartic acid/1 valine to 1.4 aspartic acid/1 valine; a molar ratio of aspartic acid/isoleucine ranges from 5.5 aspartic acid/1 isoleucine to 1.5 aspartic acid/1 isoleucine; a molar ratio of aspartic acid/threonine ranges from 5.5 aspartic acid/1 threonine to 1.7 aspartic acid/1 threonine; or a molar ratio of aspartic acid/tyrosine ranges from 40.0 aspartic acid/1 tyrosine to 9.0 aspartic acid/1 tyrosine, or any combination thereof. In embodiments thereof, the formulation further comprises at least one salt. In embodiments thereof, at least one of the free amino acids or each of the free amino acids is an L-amino acid. In embodiments thereof, promoting hydration is demonstrable by an increased rate of fluid absorption (e.g., in a perfusion assay such as those described herein or in the subject). The increased rate may be determined relative to the rate of fluid absorption of the same formulation without free amino acids. In embodiments thereof, the increased rate determined relative to the same formulation without free amino acids comprises a relative increase of at least 15%. In embodiments thereof, the increased rate determined relative to the same formulation without free amino acids comprises a relative increase ranging from 15% to 200%. In embodiments thereof, promoting intestinal barrier integrity is demonstrable by reduced measurements of intestinal permeability, decreases in transmembrane claudin-2 protein expression, and/or increases in occludin and e-cadherin proteins (e.g., in the subject) relative to these indicators of intestinal barrier function in the presence of a control formulation (e.g., water or the same formulation without free amino acids). In embodiments thereof, the formulation is formulated for administration by an enteral route (e.g., oral administration). In embodiments thereof, a formulation may be incorporated into a beverage for consumption. Suitable subjects include any animal, including a mammal. Exemplary non-mammalian animals include: reptiles and domesticated birds (e.g., chickens and turkeys). Exemplary mammals include: humans, cats, dogs, pigs, horses, cows, sheep, or goats. Such subjects may be healthy (e.g., apparently disease-free) or may be afflicted with a disease or disorder associated with dehydration or impaired barrier function. Exemplary such diseases or disorders comprise: fever, edema, incontinence, or renal failure, or any combination thereof.

In some embodiments, "6AA-Hyd" is a formulation for use in promoting hydration and/or intestinal barrier function in a subject in need thereof, wherein the formulation comprises: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid, wherein a total weight percent of free amino acids of aspartic acid ranges from 30% to 55% or 30% to 80% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote hydration or intestinal barrier integrity in the subject. In embodiments thereof, a concentration of aspartic acid ranges from 14 mM to 30 mM. In embodiments thereof, a molar ratio of aspartic acid/serine ranges from 2.8 aspartic acid/1 serine to 0.9 aspartic acid/1 serine. In embodiments thereof, a total weight percent of aspartic acid and serine is greater than a total weight percent of valine, isoleucine, threonine, and tyrosine. In embodiments thereof, the formulation does not comprise free amino acids of lysine, glycine, or tryptophan, or any combination thereof; or when present, each of the free amino acids of lysine, glycine, or tryptophan, or any combination thereof is present in a negligible amount. In embodiments thereof, the therapeutically effective combination of free amino acids consists of free amino acids of tyrosine, isoleucine, threonine, valine, serine, and aspartic acid. In embodiments thereof, the concentration of aspartic acid ranges from 15 mM to 20 mM; wherein the concentration of aspartic acid ranges from 17 mM to 20 mM; wherein the concentration of aspartic acid ranges from 18 mM to 19 mM; wherein the concentration of aspartic acid ranges from 20 mM to 30 mM; wherein the concentration of aspartic acid ranges from 25 mM to 30 mM; wherein the concentration of aspartic acid ranges from 27 mM to 30 mM; or wherein the concentration of aspartic acid ranges from 28 mM to 29 mM. In embodiments thereof, a molar ratio of aspartic acid/serine ranges from 2.8 aspartic acid/1 serine to 0.9 aspartic acid/1 serine; a molar ratio of aspartic acid/valine ranges from 3.8 aspartic acid/1 valine to 1.4 aspartic acid/1 valine; a molar ratio of aspartic acid/isoleucine ranges from 5.5 aspartic acid/1 isoleucine to 1.5 aspartic acid/1 isoleucine; a molar ratio of aspartic acid/threonine ranges from 5.5 aspartic acid/1 threonine to 1.7 aspartic acid/1 threonine; or a molar ratio of aspartic acid/tyrosine ranges from 40.0 aspartic acid/1 tyrosine to 9.0 aspartic acid/1 tyrosine, or any combination thereof. In embodiments thereof, the formulation further comprises at least one salt. In embodiments thereof, at least one of the free amino acids or each of the free amino acids is an L-amino acid. In embodiments thereof, promoting hydration is demonstrable by an increased rate of fluid absorption (e.g., in a perfusion assay such as those described herein or in the subject). The increased rate may be determined relative to the rate of fluid absorption of the same formulation without free amino acids. In embodiments thereof, the increased rate determined relative to the same formulation without free amino acids comprises a relative increase of at least 15%. In embodiments thereof, the increased rate determined relative to the same formulation without free amino acids comprises a relative increase ranging from 15% to 200%. In embodiments thereof, promoting intestinal barrier integrity is demonstrable by reduced measurements of intestinal permeability, decreases in transmembrane claudin-2 protein expression, and/or increases in occludin and e-cadherin proteins (e.g., in the subject) relative to these indicators of intestinal barrier function in the presence of a control formulation (e.g., water or the same formulation without free amino acids). In embodiments thereof, the formulation is formulated for administration by an enteral route (e.g., oral administration). In embodiments thereof, a formulation may be incorporated into a beverage for consumption. Suitable subjects include any animal, including a mammal. Exemplary non-mammalian animals include: reptiles and domesticated birds (e.g., chickens and turkeys). Exemplary mammals include: humans, cats, dogs, pigs, horses, cows, sheep, or goats. Such subjects may be healthy (e.g., apparently disease-free) or may be afflicted with a disease or disorder associated with dehydration or impaired barrier function. Exemplary such diseases or disorders comprise: fever, edema, incontinence, or renal failure, or any combination thereof.

In some embodiments, "6AA-Hyd" is a formulation for use in promoting hydration and/or intestinal barrier function in a subject in need thereof, wherein the formulation comprises: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid, wherein a total weight percent of free amino acids of aspartic acid and free amino acids of serine ranges from 50% to 85% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote hydration or intestinal barrier integrity in the subject. In embodiments thereof, a concentration of aspartic acid ranges from 14 mM to 30 mM. In embodiments thereof, a molar ratio of aspartic acid/serine ranges from 2.8 aspartic acid/1 serine to 0.9 aspartic acid/1 serine. In embodiments thereof, a total weight percent of aspartic acid and serine is greater than a total weight percent of valine, isoleucine, threonine, and tyrosine. In embodiments thereof, the formulation does not comprise free amino acids of lysine, glycine, or tryptophan, or any combination thereof; or when present, each of the free amino acids of lysine, glycine, or tryptophan, or any combination thereof is present in a negligible amount. In embodiments thereof, the therapeutically effective combination of free amino acids consists of free amino acids of tyrosine, isoleucine, threonine, valine, serine, and aspartic acid. In embodiments thereof, the concentration of aspartic acid ranges from 15 mM to 20 mM; wherein the concentration of aspartic acid ranges from 17 mM to 20 mM; wherein the concentration of aspartic acid ranges from 18 mM to 19 mM; wherein the concentration of aspartic acid ranges from 20 mM to 30 mM; wherein the concentration of aspartic acid ranges from 25 mM to 30 mM; wherein the concentration of aspartic acid ranges from 27 mM to 30 mM; or wherein the concentration of aspartic acid ranges from 28 mM to 29 mM. In embodiments thereof, a molar ratio of aspartic acid/serine ranges from 2.8 aspartic acid/1 serine to 0.9 aspartic acid/1 serine; a molar ratio of aspartic acid/valine ranges from 3.8 aspartic acid/1 valine to 1.4 aspartic acid/1 valine; a molar ratio of aspartic acid/isoleucine ranges from 5.5 aspartic acid/1 isoleucine to 1.5 aspartic acid/1 isoleucine; a molar ratio of aspartic acid/threonine ranges from 5.5 aspartic acid/1 threonine to 1.7 aspartic acid/1 threonine; or a molar ratio of aspartic acid/tyrosine ranges from 40.0 aspartic acid/1 tyrosine to 9.0 aspartic acid/1 tyrosine, or any combination thereof. In embodiments thereof, the formulation further comprises at least one salt. In embodiments thereof, at least one of the free amino acids or each of the free amino acids is an L-amino acid. In embodiments thereof, promoting hydration is demonstrable by an increased rate of fluid absorption (e.g., in a perfusion assay such as those described herein or in the subject). The increased rate may be determined relative to the rate of fluid absorption of the same formulation without free amino acids. In embodiments thereof, the increased rate determined relative to the same formulation without free amino acids comprises a relative increase of at least 15%. In embodiments thereof, the increased rate determined relative to the same formulation without free amino acids comprises a relative increase ranging from 15% to 200%. In embodiments thereof, promoting intestinal barrier function is demonstrable by reduced measurements of intestinal permeability, decreases in transmembrane claudin-2 protein expression, and/or increases in occludin and e-cadherin proteins (e.g., in the subject) relative to these indicators of intestinal barrier function in the presence of a control formulation (e.g., water or the same formulation without free amino acids). In embodiments thereof, the formulation is formulated for administration by an enteral route (e.g., oral administration). In embodiments thereof, a formulation may be incorporated into a beverage for consumption. Suitable subjects include any animal, including a mammal. Exemplary non-mammalian animals include: reptiles and domesticated birds (e.g., chickens and turkeys). Exemplary mammals include: humans, cats, dogs, pigs, horses, cows, sheep, or goats. Such subjects may be healthy (e.g., apparently disease-free) or may be afflicted with a disease or disorder associated with dehydration or impaired barrier function. Exemplary such diseases or disorders comprise: fever, edema, incontinence, or renal failure, or any combination thereof.

In some embodiments, "6AA-Hyd" is a formulation for use in promoting hydration and/or intestinal barrier function in a subject in need thereof, wherein the formulation comprises: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid, wherein a total weight percent of free amino acids of aspartic acid, free amino acids of serine, and free amino acids of valine ranges from 60% to 96% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote hydration or intestinal barrier function in the subject. In embodiments thereof, a concentration of aspartic acid ranges from 14 mM to 30 mM. In embodiments thereof, a molar ratio of aspartic acid/serine ranges from 2.8 aspartic acid/1 serine to 0.9 aspartic acid/1 serine. In embodiments thereof, a total weight percent of aspartic acid and serine is greater than a total weight percent of valine, isoleucine, threonine, and tyrosine. In embodiments thereof, the formulation does not comprise free amino acids of lysine, glycine, or tryptophan, or any combination thereof; or when present, each of the free amino acids of lysine, glycine, or tryptophan, or any combination thereof is present in a negligible amount. In embodiments thereof, the therapeutically effective combination of free amino acids consists of free amino acids of tyrosine, isoleucine, threonine, valine, serine, and aspartic acid. In embodiments thereof, the concentration of aspartic acid ranges from 15 mM to 20 mM; wherein the concentration of aspartic acid ranges from 17 mM to 20 mM; wherein the concentration of aspartic acid ranges from 18 mM to 19 mM; wherein the concentration of aspartic acid ranges from 20 mM to 30 mM; wherein the concentration of aspartic acid ranges from 25 mM to 30 mM; wherein the concentration of aspartic acid ranges from 27 mM to 30 mM; or wherein the concentration of aspartic acid ranges from 28 mM to 29 mM. In embodiments thereof, a molar ratio of aspartic acid/serine ranges from 2.8 aspartic acid/1 serine to 0.9 aspartic acid/1 serine; a molar ratio of aspartic acid/valine ranges from 3.8 aspartic acid/1 valine to 1.4 aspartic acid/1 valine; a molar ratio of aspartic acid/isoleucine ranges from 5.5 aspartic acid/1 isoleucine to 1.5 aspartic acid/1 isoleucine; a molar ratio of aspartic acid/threonine ranges from 5.5 aspartic acid/1 threonine to 1.7 aspartic acid/1 threonine; or a molar ratio of aspartic acid/tyrosine ranges from 40.0 aspartic acid/1 tyrosine to 9.0 aspartic acid/1 tyrosine, or any combination thereof. In embodiments thereof, the formulation further comprises at least one salt. In embodiments thereof, at least one of the free amino acids or each of the free amino acids is an L-amino acid. In embodiments thereof, promoting hydration is demonstrable by an increased rate of fluid absorption (e.g., in a perfusion assay such as those described herein or in the subject). The increased rate may be determined relative to the rate of fluid absorption of the same formulation without free amino acids. In embodiments thereof, the increased rate determined relative to the same formulation without free amino acids comprises a relative increase of at least 15%. In embodiments thereof, the increased rate determined relative to the same formulation without free amino acids comprises a relative increase ranging from 15% to 200%. In embodiments thereof, promoting intestinal barrier function is demonstrable by reduced measurements of intestinal permeability, decreases in transmembrane claudin-2 protein expression, and/or increases in occludin and e-cadherin proteins (e.g., in the subject) relative to these indicators of intestinal barrier function in the presence of a control formulation (e.g., water or the same formulation without free amino acids). In embodiments thereof, the formulation is formulated for administration by an enteral route (e.g., oral administration). In embodiments thereof, a formulation may be incorporated into a beverage for consumption. Suitable subjects include any animal, including a mammal. Exemplary non-mammalian animals include: reptiles and domesticated birds (e.g., chickens and turkeys). Exemplary mammals include: humans, cats, dogs, pigs, horses, cows, sheep, or goats. Such subjects may be healthy (e.g., apparently disease-free) or may be afflicted with a disease or disorder associated with dehydration or impaired barrier function. Exemplary such diseases or disorders comprise: fever, edema, incontinence, or renal failure, or any combination thereof.

In some embodiments, a formulation for use in promoting hydration or promoting intestinal barrier function comprises at least one salt. In some embodiments, the at least one salt is a sodium salt. Exemplary sodium salts include, for example, NaCl, and mono-, di-, or tri-sodium citrate. In some embodiments, the formulation for use in promoting hydration comprises more than one sodium salt. In some embodiments, the formulations comprise at least 0.5 mM Na, at least 5 mM Na, at least 10 mM Na, at least 15 mM Na, at least 20 mM Na, at least 30 mM Na, at least 40 mM Na, at least 50 mM Na, at least 60 mM Na, or at least 70 mM Na. In some embodiments, the formulations comprise a range of 0.5 mM-50 mM Na, a range of 5 mM-50 mM Na, a range of 10 mM-50 mM Na, a range of 15 mM-50 mM Na, a range of 20 mM-50 mM Na, a range of 25 mM-50 mM Na, a range of 30 mM-50 mM Na, or a range of 40 mM-50 mM Na. In some embodiments, the formulations comprise a range of 0.5 mM-30 mM Na, a range of 5 mM-30 mM Na, a range of 10 mM-30 mM Na, a range of 15 mM-30 mM Na, a range of 20 mM-30 mM Na, or a range of 25 mM-30 mM Na. In some embodiments, the formulations comprise a range of 0.5 mM-25 mM Na, a range of 5 mM-25 mM Na, a range of 10 mM-25 mM Na, a range of 15 mM-25 mM Na, a range of 15 mM-20 mM Na, or a range of 20 mM-25 mM Na. In some embodiments, the formulations comprise 15 mM Na, 16 mM Na, 17 mM Na, 18 mM Na, 19 mM Na, or 20 mM Na. Other exemplary salts include, potassium citrate and magnesium citrate.

Ringer's Solution with 17 mM Na Comprises the Following in Water:

|  | Osm |
|---|---|
| NaCl | 11 |
| KCl | 5.2 |
| CaCl$_2$ | 1.2 |
| MgCl$_2$ | 1.2 |
| Tri Sodium Citrate | 2 |

In an exemplary embodiment, the "6AA-Hyd" formulation comprises the following formulation in Ringer's solution with 17 mM Na and is a formulation for use in promoting hydration or intestinal barrier function in a subject in need thereof, wherein the formulation comprises: a therapeutically effective amount of a combination of free amino acids, wherein the combination of free amino acids consists essentially of or consists of tyrosine, isoleucine, threonine, valine, serine, and aspartic acid; wherein a concentration of aspartic acid ranges from 14 mM to 30 mM; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; wherein the molar ratio of aspartic acid/isoleucine ranges from 5.5 aspartic acid/1 isoleucine to 1.5 aspartic acid/1 isoleucine; wherein the molar ratio of aspartic acid/threonine ranges from 5.5 aspartic acid/1 threonine to 1.7 aspartic acid/1 threonine; wherein the molar ratio of aspartic acid/tyrosine ranges from 40.0 aspartic acid/1 tyrosine to 9.0 aspartic acid/1 tyrosine; wherein the therapeutically effective combination of free amino acids is sufficient to promote hydration in the subject. The total weight percent of free amino acids of aspartic acid ranges from 30% to 55% of a total weight of the therapeutically effective combination of free amino acids.

The "8AA" formulation comprises the following formulation in Ringer's solution with 17 mM Na and is a comparator formulation, wherein the formulation comprises: a therapeutically effective combination of free amino acids, wherein the therapeutically effective combination of free amino acids consists essentially of lysine, aspartic acid, glycine, isoleucine, threonine, tyrosine, valine, and serine; and wherein a concentration of aspartic acid is 8 mM; and wherein a molar ratio of aspartic acid/serine is 0.8 aspartic acid/1 serine. The total weight percent of free amino acids of aspartic acid ranges from 15% to 16% of a total weight of the therapeutically effective combination of free amino acids.

Based on results presented herein, 6AA-Hyd was selected as an exemplary formulation of the present invention that exhibits substantial and significant increases in fluid absorption rate relative to the same formulation without free amino acids in single-pass intestinal perfusion assays performed in rats, which assays serve as a model system that recapitulates features of hydration as described herein. Results presented herein are briefly presented below as follows:

At 15-90 minutes of perfusion, the fluid absorption rate of 6AA-Hyd was about 2.3 times (about 131%) more than that of the Control solution [Control (Ringer's saline with 17 mM Na); the same formulation without free amino acids]. See FIG. 1. The difference in absorption rate between 6AA-Hyd and Control was statistically significant as reflected by, for example, the error bars presented in FIG. 1.

Figure 2:
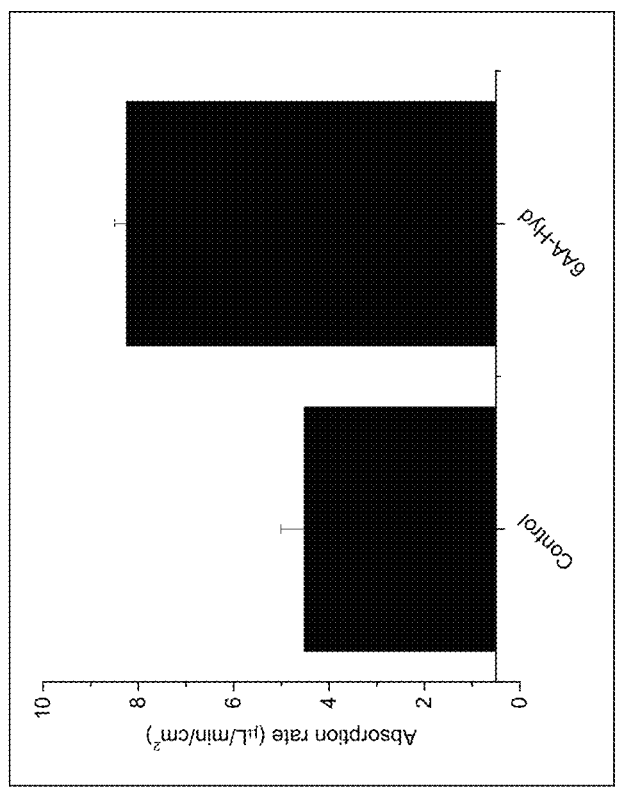
FIG. 2: Absorption rate as determined using a single-pass intestinal perfusion assay in rats at 105-180 minutes incubation time. Control (Ringer's saline with 17 mM Na); 6AA-Hyd. The difference observed between Control vs. 6AA-Hyd is statistically significant as reflected by $P<0.05$.

A significant differential between 6AA-Hyd and Control persisted even at 105-180 minutes of perfusion. Indeed, the absorption rate of 6AA-Hyd was about 1.8 times (about 83%) more than that of the Control solution [Control (Ringer's saline with 17 mM Na)] at 105-180 minutes of perfusion. See FIG. 2. The difference in absorption rate between 6AA-Hyd and Control was statistically significant as reflected by, for example, the error bars presented in FIG. 2.

TABLE 1

Figure 3A:
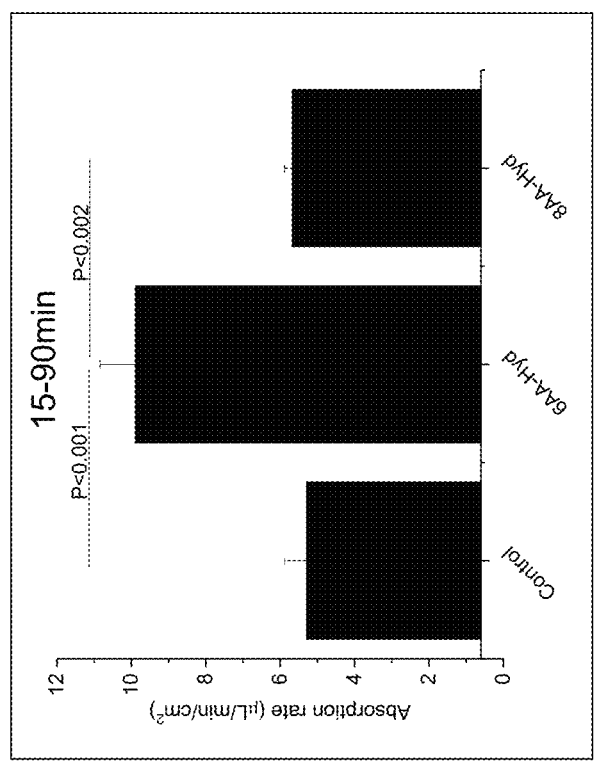
FIG. 3A and FIG. 3B: Absorption rate as determined using a single-pass intestinal perfusion assay in rats at 15-90 minutes incubation time (FIG. 3A) or 105-180 minutes incubation time (FIG. 3B). Control (Ringer's saline with 17 mM Na); 6AA-Hyd; and 8AA (Ringer's saline with 17 mM Na with lysine, aspartic acid, glycine, isoleucine, threonine, tyrosine, valine, and serine). The difference in absorption rate observed between Control and each of 6AA-Hyd and 8AA is statistically significant. The difference in absorption rate observed between 6AA-Hyd and 8AA at either of 15-90 minutes incubation time or 105-180 minutes incubation time is statistically significant.
Figure 3B:
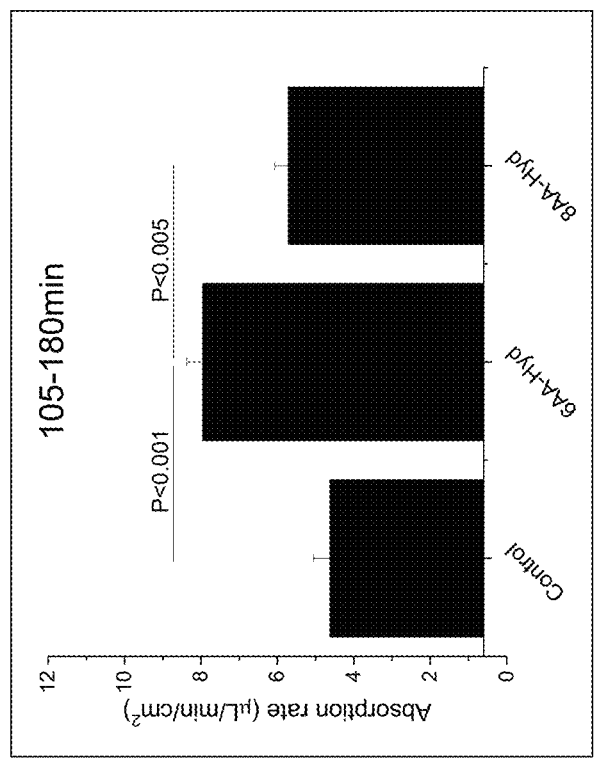

Additional details relating to results of perfusion studies depicted graphically in FIG. 3A and 3B.

| | 15-90 Minutes | | | 105-180 Minutes | | |
|---|---|---|---|---|---|---|
| | Control | 6AA-Hyd | 8AA | Control | 6AA | 8AA |
| Mean | 5.29 | 9.89 | 5.67 | 4.62 | 7.95 | 5.71 |
| SEM | 0.58 | 0.95 | 0.21 | 0.43 | 0.42 | 0.36 |
| N | 6 | 11 | 4 | 10 | 13 | 10 |

Standard Error of the Mean (SEM); Number of Animals (N)

As shown in FIG. 3A, the fluid absorption rate of 6AA-Hyd was about 1.9 times (about 87%) more than that of the Control solution [Control (Ringer's saline with 17 mM Na); the same formulation without free amino acids] at 15-90 minutes of perfusion. The difference in absorption rate between 6AA-Hyd and Control was statistically significant as reflected by, for example, the error bars presented in FIG. 3A and the indicated P-value, which value is considered highly significant. FIG. 3A also shows that 6AA-Hyd exhibited an absorption rate that was about 1.7 times (about 74%) more than that of 8AA following 15-90 minutes of perfusion; this result is statistically significant as indicated by the error bars and P-value shown.

As shown in FIG. 3B, the fluid absorption rate of 6AA-Hyd was about 1.7 times (about 72%) more than that of the Control solution [Control (Ringer's saline with 17 mM Na); the same formulation without free amino acids] at 105-180 minutes of perfusion. The difference in absorption rate between 6AA-Hyd and Control was statistically significant as reflected by, for example, the error bars presented in FIG. 3B and the indicated P-value, which value is considered highly significant. FIG. 3B also shows that 6AA-Hyd exhibited an absorption rate that was about 1.4 times (about 39%) more than that of 8AA following 105-180 minutes of perfusion; this result is statistically significant as indicated by the error bars and P-value shown.

Figure 4:
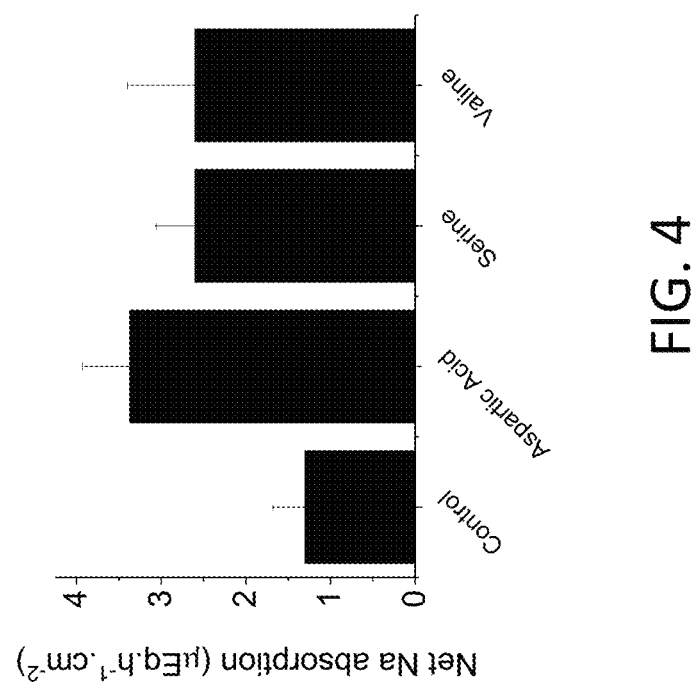
FIG. 4: Net sodium (Na) absorption associated with single amino acids of 6AA-Hyd. The difference observed between Control and each of the indicated amino acids is statistically significant.

An increase in sodium absorption, which is an indicator of fluid absorption, may be determined by, for example, measuring benzamil/amiloride sensitive current in an Ussing chamber. Increased net sodium absorption is associated with increased net water absorption whereby water diffuses through the intercellular space into the circulation in response to the osmotic sodium gradient established by, for example, the sodium-hydrogen exchanger 3 (NHE3) and/or amino acid cotransport. Increased sodium absorption is associated with increased NHE3 expression at the apical membrane and sodium-coupled amino acid transport. As shown in FIG. 4, net sodium absorption conferred by each of free amino acids of aspartic acid, serine, and valine is significantly higher than that of control solution.

Figure 5:
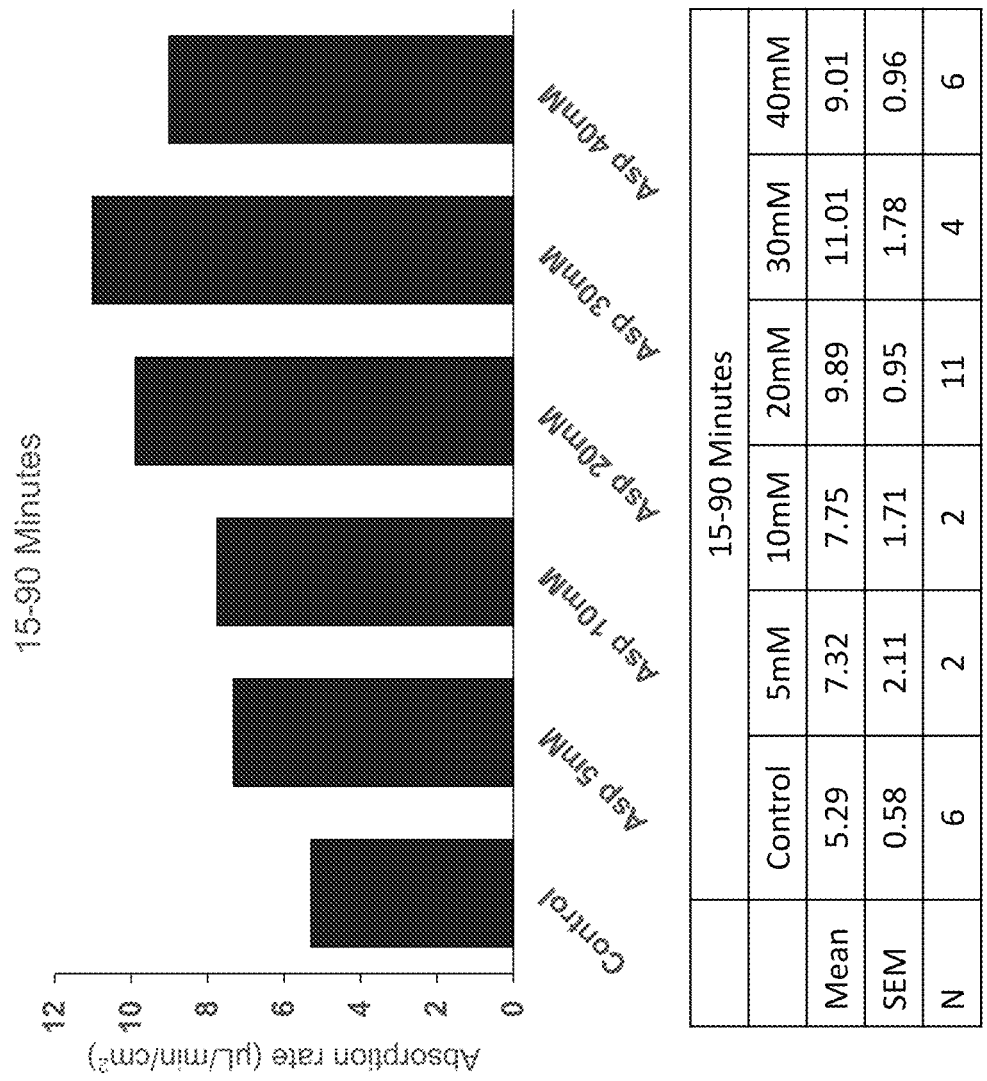
FIG. 5: Absorption rate as determined using a single-pass intestinal perfusion assay in rats at 15-90 minutes incubation time. Control (formulation without free amino acids); 5 mM aspartic acid (Asp); 10 mM Asp; 20 mM Asp; 30 mM Asp; and 40 mM Asp. Each of the 5 mM, 10 mM, 20 mM, 30 mM, and 40 mM Asp formulations comprised all six amino acids of 6AA-Hyd; the ratio of Asp to serine was constant among the 5 mM, 10 mM, 20 mM, 30 mM, and 40 mM Asp formulations; the ratio of Asp to valine was constant among the 5 mM, 10 mM, 20 mM, 30 mM, and 40 mM Asp formulations; the ratio of Asp to threonine was constant among the 5 mM, 10 mM, 20 mM, 30 mM, and 40 mM Asp formulations; the ratio of Asp to tyrosine was constant among the 5 mM, 10 mM, 20 mM, 30 mM, and 40 mM Asp formulations; and the ratio of Asp to isoleucine was constant among the 5 mM, 10 mM, 20 mM, 30 mM, and 40 mM Asp formulations. Abbreviations: standard error of the mean (SEM); and number of animals (N).

FIG. 5 presents a histogram plot depicting fluid absorption rate as determined using a single-pass intestinal perfusion assay in rats at 15-90 minutes incubation time. FIG. 5 shows a trend toward higher fluid absorption rates at higher concentrations of aspartic acid (Asp). Peak Asp-induced fluid absorption rate is observed in the range of 14 mM to 30 mM Asp as revealed by maximal fluid absorption rates at 20 mM Asp and 30 mM Asp. FIG. 5 further shows that the fluid absorption rate is declining by 40 mM Asp. These results reveal that peak fluid absorption rate is associated with a concentration of Asp ranging from about 14 mM to 30 mM.

In some embodiments, a concentration of each of the free amino acids present in 6AA-Hyd ranges from 0.1 mM to 30 mM or 0.5 mM to 30 mM. In some embodiments, a concentration of each of the free amino acids present in a formulation ranges from 0.1 mM to 20 mM or 0.5 mM to 20 mM. In some embodiments, a concentration of each of free amino acids of aspartic acid, serine, valine, isoleucine, and threonine present in the formulation ranges from 5 mM to 30 mM. In some embodiments, a concentration of each of free amino acids of aspartic acid, serine, and valine present in the formulation ranges from 8 mM to 30 mM. In some embodiments, a concentration of each of free amino acids of aspartic acid and serine present in the formulation ranges from 10 mM to 30 mM. In some embodiments, a concentration of each of free amino acids of aspartic acid and serine present in the formulation ranges from 10 mM to 20 mM.

In some embodiments, the pH of 6AA-Hyd ranges from 2.0 to 8.0, 2.5 to 8.0, 3.0 to 8.0, 3.5 to 8.0, 4.0 to 8.0, 4.5 to 8.0, 5.0 to 8.0, 5.5 to 8.0, 6.0 to 8.0, 6.5 to 8.0, 7.0 to 8.0, 7.5 to 8.0, 2.0 to 3.0, 2.5 to 4.0; 3.0 to 4.0; 3.3 to 3.8, or is about 2.5, 2.6, 2.9, 3.4, or 3.8.

As used herein, the phrase "increased rate of fluid absorption" may be used to refer to an increase in fluid absorption rate of 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 300%, 400%, or 500% as measured using a single-pass intestinal perfusion assay in rats, wherein the increased rate is determined relative to the same formulation without free amino acids and wherein the increased rate may be determined at 15-90 minutes of perfusion.

As used herein, the phrase "increased rate of fluid absorption" may be used to refer to an increase in fluid absorption rate of one-fold, two-fold, three-fold, four-fold, five-fold, six-fold, seven-fold, eight-fold, nine-fold, ten-fold, fifteen-fold, twenty-fold, thirty-fold, forty-fold, or fifty-fold as measured using a single-pass intestinal perfusion assay in rats, wherein the increased rate is determined relative to the same formulation without free amino acids and wherein the increased rate may be determined at 15-90 minutes of perfusion.

As used herein, the phrase "promoting hydration" may be used to reflect an increase in fluid absorption rate of 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 300%, 400%, or 500% as measured using a single-pass intestinal perfusion assay in rats, wherein the increased rate is determined relative to the same formulation without free amino acids and wherein the increased rate may be determined at 15-90 minutes of perfusion.

As used herein, the phrase "promoting hydration" may be used to reflect an increase in fluid absorption rate of one-fold, two-fold, three-fold, four-fold, five-fold, six-fold, seven-fold, eight-fold, nine-fold, ten-fold, fifteen-fold, twenty-fold, thirty-fold, forty-fold, or fifty-fold as measured using a single-pass intestinal perfusion assay in rats, wherein the increased rate is determined relative to the same formulation without free amino acids and wherein the increased rate may be determined at 15-90 minutes of perfusion.

As used herein, the term "healthy subject" may be used to refer to a subject who has not been diagnosed with an acute medical condition. In some embodiments, the healthy subject is a healthy human. Healthy humans may encompass, for example, athletes of any level and/or age (ranging from amateur to professional), military personnel, older persons (e.g., persons 65 years or older), or workers exposed to adverse conditions (such as extreme heat) who want to maintain or restore hydration levels and/or maintain or restore intestinal barrier function.

As described herein, an increase in fluid absorption or fluid absorption rate may be determined by, for example, measuring fluid uptake in a single-pass intestinal perfusion assay in rats. An increase in sodium absorption, which is an indicator of fluid absorption, may be determined by, for example, measuring benzamil/amiloride sensitive current in an Ussing chamber.

Based on results presented herein, 6AA-Hyd was selected as an exemplary formulation that exhibits substantial and significant increases in fluid absorption rate relative to a control solution (the same formulation without free amino acids) in a model system described herein wherein intestinal fluid absorption can be quantitated.

As described herein, formulations described herein may be in powder form or liquid form. Accordingly, in some embodiments, formulations described herein may be powder formulations or liquid formulations.

The present inventors have established a model system in which to evaluate net fluid absorption rate in the context of a mammalian intestine. More particularly, an anesthetized rat model for intestinal lumen perfusion has been developed (a single-pass intestinal perfusion assay in rats) that may be used to quantitate intestinal fluid absorption, particularly fluid absorption rate. The ability to detect and quantitate rapid fluid absorption rate is useful in the context of evaluating rehydration solutions such as, for example, 6AA-Hyd, at least because rapid fluid absorption rate is a desirable feature of rehydration solutions. When such a rehydration solution as described herein is consumed for the purpose of maintaining or restoring normal hydration levels in a healthy subject, rapid fluid absorption rate, which in turn results in rapid rehydration, is a desired objective. Alternatively, when such a rehydration solution as described herein is consumed for the purpose of maintaining or restoring normal hydration level in a subject afflicted with a disease or disorder associated with dehydration, rapid fluid absorption rate, which in turn results in rapid rehydration, is a desired, even urgent, objective. As described herein, one method of determining rapid rehydration is a determination of fluid absorption rate, which may be detected within the first 15-90 minutes and/or the first 105-180 minutes following initiation of perfusion in a single-pass intestinal perfusion assay in rats. Indeed, results derived from 15-90 minute time points following initiation of perfusion in a single-pass intestinal perfusion assay in rats are most relevant with respect to fluid absorption rate, which in turn translates to rapid rehydration for the time period.

Based on results presented herein, 6AA-Hyd was selected as an exemplary formulation that exhibits the ability to increase intestinal fluid absorption rate rapidly (e.g., within 15-90 minutes of perfusion initiation in a single-pass intestinal perfusion assay in rats) relative to a control solution (Ringer solution with 17 mM NaCl; the same formulation without free amino acids) and exhibits a statistically significant increase in intestinal fluid absorption rate when compared to different amino acid formulations (e.g., 8AA). The superiority of 6AA-Hyd relative to 8AA with respect to its ability to increase intestinal fluid absorption rate at 15-90 minutes or 105-180 minutes of perfusion is shown in, for example, FIGS. 3A-3B.

As described herein, a rapid increase in intestinal fluid absorption rate may be determined by, for example, measuring fluid absorption in a single-pass intestinal perfusion assay in rats within 15-90 minutes of perfusion and/or 105-180 minutes of perfusion. A quantitative measurement made for a particular formulation within, for example, 15-90 minutes of perfusion may be compared to the fluid absorption of a control solution (e.g., Ringer solution with 17 mM NaCl; the same formulation without free amino acids) measured at the same perfusion time frame to determine percent increase relative to the control solution. See, for example, FIGS. 1, 2, 3A and 3B. A quantitative measurement made for a particular formulation may, furthermore, be compared to the fluid absorption rate of, for example, test formulations measured within 15-90 minutes of perfusion and/or 105-180 minutes of perfusion as a relative comparator to identify formulations having enhanced properties with respect to the ability to increase the rate of intestinal fluid uptake. A quantitative measurement made for a particular formulation may, furthermore, be compared to fluid absorption rate of, for example, a positive control formulation measured within 15-90 minutes of perfusion and/or 105-180 minutes of perfusion as a relative comparator predictive of efficacy for treating a disease or disorder associated with dehydration.

Barrier function: The intestinal epithelium is composed of a single layer of cells bound together by tight junctions. The intestinal epithelium provides two critical functions: it allows passage and absorption of nutrients, water, and ions; and it forms a highly regulated barrier that separates the body from harmful luminal content, such as toxins, microorganisms, and antigens. In addition, stressors such as non-steroidal anti-inflammatory drugs (NSAIDs), exercise, and irradiation can cause a temporary 'open window' opportunity for local and systemic inflammation responses to occur. By maintaining and/or restoring function to the intestinal epithelial barrier, the stringent criteria for selective permeability are upheld and pathological leakiness of and infiltration across the intestinal epithelium are minimized or prevented.

Tight junctions contribute substantially to maintaining barrier function in intact epithelia. Tight junctions comprise a complex network of transmembrane, cytosolic, cytoskeletal, and regulatory proteins. Two distinct pathways, designated pore and leak, regulate paracellular flux in intact epithelia. Unrestricted flux pathway predominates in ulcerated or denuded epithelia. Reduced intestinal epithelial barrier function is associated with some gastrointestinal [e.g., inflammatory bowel disease (IBD)] and systemic (e.g., graft versus host disease) diseases, but is insufficient to cause disease absent additional triggers. Experimental evidence from mouse models of experimental colitis (a type of IBD) has revealed that increased paracellular permeability accelerates experimental colitis and that preservation of tight junction barrier function delays disease progression. No currently available therapeutics specifically modulate epithelial barrier function. Accordingly, amino acid formulations described herein which maintain and/or restore barrier function provide for an unmet therapeutic need.

Tight junction integrity contributes substantially to barrier function and improvement in tight junction integrity is associated with reduced measurements of intestinal permeability. Adherens junctions and desmosomes provide the adhesive forces necessary for maintenance of cell—cell interactions. The cadherins, which are single spanning transmembrane proteins that interact homotypically with the extracellular portion of cadherins on adjacent cells, are components of adherens junctions. Cadherins interact directly with the cytoplasmic proteins p120 catenin and β-catenin, which in turn interact with α-catenin. α-catenin regulates perijunctional actin assembly, thereby strengthening protein-protein interactions. Adherens junctions are, furthermore, necessary for efficient tight junction assembly, a function that in vitro studies have attributed to both epithelial cadherin (E-cadherin) and α-catenin. Indeed, increases in E-cadherin and occludin proteins may be viewed as indicative of restoration of or improvement in tight junction integrity. Improvements in crypt and villus morphology and LGR5+ stem cell proliferation are also positive indicators of barrier restoration in damaged epithelia and curtailment of the unrestricted flux pathway. Tight junction integrity is also associated with decreases in claudin-2 protein expression and function. Accordingly, improvement in tight junction integrity as indicated by at least one of a reduction in intestinal permeability; an increase in E-cadherin expression and/or activity; an increase in occludin protein expression or activity; a decrease in claudin-2 protein expression or function; or any combination thereof provides a positive indicator of therapeutic efficacy conferred by amino acid formulations described herein. Such increases and decreases may be determined relative to a negative control such as, for example, water or the same solution in which the amino acid formulation was made, but without the free amino acids.

As used herein, the term "intestinal barrier function" refers to the property of the intestinal mucosa that ensures adequate containment of antigenic luminal contents within the intestinal lumen, preventing translocation of these harmful luminal contents to the systemic compartment, while preserving the ability to absorb nutrients and performing the functions of the gastrointestinal mucosa. The term may also be used to refer to the ability of a single cell layer of intestinal epithelium to exhibit selectively permeable functions (i.e., adequate containment of undesirable luminal contents within the intestine while preserving the ability to absorb nutrients).

As used herein, the term "intestinal barrier integrity" refers to adequate containment of antigenic luminal contents within the intestinal lumen, preventing translocation of these harmful luminal contents to the systemic compartment. The term may also be used to refer to the degree to which intestinal barrier function is properly maintained.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. The phrases "effective amount" and "therapeutically effective amount" are used interchangeably. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. In some embodiments, an effective amount is an amount that increases the fluid absorption rate in a cell. In some embodiments, an effective amount is an amount that promotes hydration by rapidly increasing the fluid absorption rate in a subject in need thereof. In some embodiments, an effective amount is an amount that reduces the symptoms of and/or treats a disease or disorder associated with dehydration by rapidly increasing the fluid absorption rate in the subject.

"Treat," "treatment", "treating" and similar terms as used herein in the context of treating a subject refer to providing medical and/or surgical management of a subject. Treatment may include, but is not limited to, administering an agent or composition (e.g., a pharmaceutical composition) to a subject. The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The effect of treatment may also include reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments, a therapeutic agent may be administered to a subject who has had a disease but no longer shows evidence of the disease. The agent may be administered, e.g., to reduce the likelihood of recurrence of the disease. A therapeutic agent may be administered prophylactically, i.e., before development of any symptom or manifestation of a disease.

"Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease).

The term "amelioration" or any grammatical variation thereof (e.g., ameliorate, ameliorating, and amelioration, etc.), as used herein, includes, but is not limited to, delaying the onset, or reducing the severity of a disease or condition (e.g., disease or disorder associated with dehydration or a complication thereof). Amelioration, as used herein, does not require the complete absence of symptoms.

The terms "condition," "disease," and "disorder" are used interchangeably.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g. humans; non-human primates (e.g., apes, chimpanzees, orangutans, monkeys); domesticated animals such as dogs, cats, rabbits, cattle, oxen, horses, pigs, sheep, goats, chicken, turkeys, llamas, mice, and rats. In some embodiments, the subject is a human. The human may be of either sex and may be at any stage of development. In some embodiments, the subject is exposed to climate conditions (e.g., extreme heat) that lead to excessive sweating that can, in turn, lead to varying degrees of dehydration.

In some embodiments, the subject has been diagnosed with a disease or disorder associated with dehydration. In some embodiments, the human or other mammal is an elderly subject (e.g., a human equal to or over the age of 70 years). In some embodiments, an elderly subject may exhibit decreased fluid intake relative to a recommended intake suggested by a medical practitioner attending to the elderly subject or standards set by the medical establishment. In some embodiments, the subject has been diagnosed with a disease or disorder associated with dehydration, including without limitation: a fever; edema, which results in increased loss of fluids into abdominal cavities or organs (such as that observed with peritonitis); incontinence (particularly in humans equal to or over the age of 70 years), which results in increased loss of fluids via increased urine production; and/or renal failure.

By "negligible amount" it is meant that the amino acid present does not rapidly increase the fluid absorption rate in, for example, a single pass intestinal perfusion in rats. Or, in some embodiments, even if the amino acid is present in the formulation, it is not present in an amount that would affect the fluid absorption rate in, for example, a single pass intestinal perfusion in rats or the therapeutic effect of treating a subject in need thereof. In some embodiments, a negligible amount is an amount wherein the total concentration of the amino acid is less than 100 mg/l, 50 mg/l, 10 mg/l, 5 mg/l, 1 mg/l, 0.5 mg/l, 0.1 mg/l, or 0.01 mg/l. In some embodiments, a negligible amount is an amount wherein the total concentration of the amino acid is less than 100 mg/l. In some embodiments, a negligible amount is an amount wherein the total concentration of the amino acid is less than 50 mg/l. In some embodiments, a negligible amount is an amount wherein the total concentration of the amino acid is less than 10 mg/l. In some embodiments, a negligible amount is an amount wherein the total concentration of the amino acid is less than 5 mg/l. In some embodiments, a negligible amount is an amount wherein the total concentration of the amino acid is less than 1 mg/l. In some embodiments, a negligible amount is an amount wherein the total concentration of the amino acid is less than 0.5 mg/l. In some embodiments, a negligible amount is an amount wherein the total concentration of the amino acid is less than 0.1 mg/l. In some embodiments, a negligible amount is an amount wherein the total concentration of the amino acid is less than 0.01 mg/l.

In some embodiments, a negligible amount of lysine is less than 1 mM, a negligible amount of glycine is less than 0.5 mM, and/or a negligible amount of glycine is less than 0.5 mM.

The term "amino acid" encompasses all known amino acids comprising an amine ($—NH_2$) functional group, a carboxyl (—COOH) functional group, and a side chain ("R") group specific to each amino acid. "Amino acids" encompasses the 21 amino acids encoded by the human genome (i.e., proteinogenic amino acids), amino acids encoded or produced by bacteria or single-celled organisms, and naturally derived amino acids. For the purposes of this disclosure, the conjugate acid form of amino acids with basic side chains (arginine, lysine, and histidine) or the conjugate base form of amino acids with acidic side chains (aspartic acid and glutamic acid) are essentially the same, unless otherwise noted. "Amino acids" also encompass derivatives thereof that retain substantially the same activity in terms of promoting hydration in, for example, a single pass intestinal perfusion in rats. The derivatives may be, for example, enantiomers, and include both the D- and L-forms of the amino acids. The derivatives may be derivatives of "natural" or "non-natural" amino acids (e.g., β-amino acids, homo-amino acids, proline derivatives, pyruvic acid derivatives, β-substituted alanine derivatives, glycine derivatives, ring-substituted tyrosine derivatives, ring-substituted phenylalanine derivatives, linear core amino acids, and N-methyl amino acids), for example, selenocysteine, pyrrolysine, iodotyrosine, norleucine, or norvaline. Other amino acid derivatives include, but are not limited to, those that are synthesized by, for example, acylation, methylation, glycosylation, and/or halogenation of the amino acid. These include, for example, O-methyl amino acids, C-methyl amino acids, and N-methyl amino acids. The amino acids described herein may be present as free amino acids. The term "free amino acid" refers to an amino acid that is not part of a peptide or polypeptide (e.g., is not connected to another amino acid through a peptide bond). A free amino acid is free in solution, but may be associated with a salt or other component in solution.

As used herein, the term "salt" refers to any and all salts and encompasses pharmaceutically acceptable salts.

The term "carrier" may refer to any diluent, adjuvant, excipient, or vehicle with which a formulation described herein is administered. Examples of suitable pharmaceutical carriers are described in Remington's Essentials of Pharmaceuticals, 21$^{st}$ ed., Ed. Felton, 2012, which is herein incorporated by reference.

Exemplary salts for inclusion in a formulation described herein include sodium chloride, potassium chloride, calcium chloride, magnesium chloride, tri-sodium citrate, sodium bicarbonate, sodium gluconate phosphate buffers using mono, di or tri-sodium phosphate, or any combination thereof.

Electrolytes are substances that dissociate in solution and have the ability to conduct an electrical current. Electrolytes are either cations (positively charged) or anions (negatively charged). Dissolution of a salt in a solvent such as, for example, water results in a solution of electrolytes, since the component ions of the salt dissociate in a process called solvation. When sodium chloride or table salt is added to water, for example, the salt dissolves and breaks down into its component ions sodium (Na+) and chloride (Cl−). As used herein, when referring to a salt in solution, it is understood that the term salt relates to the term electrolyte in light of the chemical relationship between a salt and its component ions.

Exemplary diluents include calcium carbonate, sodium carbonate, calcium phosphate, dicalcium phosphate, calcium sulfate, calcium hydrogen phosphate, cellulose, microcrystalline cellulose, kaolin, amylase resistant starch, and mixtures thereof.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The exact amount of an amino acid formulation required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In some embodiments, when multiple doses are administered to a subject or applied to a tissue or cell, any two doses of the multiple doses include different or substantially the same amounts of an amino acid composition described herein. In some embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In some embodiments, the frequency of administering the multiple doses to the subject or applying the multiple doses to the tissue or cell is one dose per day. In some embodiments, the frequency of administering the multiple doses to the subject or applying the multiple doses to the tissue or cell is two doses per day. In some embodiments, the frequency of administering the multiple doses to the subject or applying the multiple doses to the tissue or cell is three doses per day. In some embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In some embodiments, the duration between the first dose and last dose of the multiple doses is three months, six months, or one year. In some embodiments, the duration between the first dose and last dose of the multiple doses is the lifetime of the subject, tissue, or cell.

In some embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, between 1 g and 10 g, between 1 g and 15 g, or between 1 g and 20 g, inclusive, of an amino acid composition described herein. In some embodiments, a dose described herein includes independently between 1 mg and 3 mg, inclusive, of an amino acid composition described herein. In some embodiments, a dose described herein includes independently between 3 mg and 10 mg, inclusive, of an amino acid composition described herein. In some embodiments, a dose described herein includes independently between 10 mg and 30 mg, inclusive, of an amino acid composition described herein. In some embodiments, a dose described herein includes independently between 30 mg and 100 mg, inclusive, of an amino acid composition described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Diseases or disorders associated with dehydration, include without limitation: a fever [Center for Disease Control considers a person to have a fever if his/her temperature equals or exceeds 100.4° F. (38° C.)]; edema, which results in increased loss of fluids into abdominal cavities or organs (such as that observed with peritonitis); incontinence (particularly in humans equal to or over the age of 70 years), which results in increased loss of fluids via increased urine production; and/or renal failure.

In some embodiments, an amino acid formulation described herein is incorporated into a beverage for consumption. In some embodiments, 6AA-Hyd or at least one of each of the 6 amino acids in 6AA-Hyd is added as a dry powder to a solution comprising salts and desired flavoring agents and dissolved in the solution by mixing to generate a functional beverage. Such functional beverages exhibit beneficial properties conferred by inclusion of 6AA-Hyd. Examples of such beneficial properties include the ability to promote hydration and/or intestinal barrier function in a subject who has consumed the functional beverage. In short, the volume of the solution is adjusted to offset for the volume of 6AA-Hyd added so as to achieve a desired final concentration of each of the six amino acids in the functional beverage, as well as any salts or desired flavoring agents present in the solution. The adjustment in volume is achieved by reducing the amount of water relative to other components in the solution so as to adjust for the volumetric changes that result from addition of 6AA-Hyd.

In exemplary embodiments, 1-15 g, 1-12.5 g, 1-10 g, 1-7.5 g, or 1-5 g of 6AA-Hyd is added to a solution to generate a functional beverage comprising salts and flavoring agents. In exemplary embodiments, a functional beverage generated has a serving size of 16-30 ounces (oz) and is packaged in a suitable container. In exemplary embodiments, a functional beverage generated has a serving size of 20 oz and is packaged in a suitable container.

Functional beverages are assessed based on a sensory profile for acceptability. Considerations for sensory profiles include: taste, shelf life, flavor strength, sweetness, bitterness, smell, and appearance. The pH of the solution into which 6AA-Hyd is added to make the functional beverage or the functional beverage may be adjusted to match the desired flavor profile. Additional compounds such as aroma flavors, masking agents, and/or dyes may be incorporated into the solution into which 6AA-Hyd is added to make the functional beverage or the functional beverage to achieve desired sensory profile objectives.

All prior patents, publications, and test methods referenced herein are incorporated by reference in their entireties.

DETAILED DESCRIPTION OF SOME EMBODIMENTS

6AA-Hyd is an exemplary formulation described herein. For the sake of simplicity, each of the select amino acids is referred to with the standard single capital letters for amino acids as follows: aspartic acid (D), serine (S), valine (V), isoleucine (I), threonine (T) and tyrosine (Y).

In some embodiments, the formulation comprises, consists essentially of, or consists of free amino acids of aspartic acid (D) and serine (S) and free amino acids of at least one of valine (V), isoleucine (I), threonine (T) or tyrosine (Y), wherein a concentration of aspartic acid ranges from 14 mM to 30 mM; and wherein a molar ratio of aspartic acid/serine ranges from 2.8 aspartic acid/1 serine to 0.9 aspartic acid/1 serine. The different combinations of this embodiment are presented in List 1 as follows: Six AA: D, S, V, I, T, and Y; Five AA subsets: D, S, V, I, and T; D, S, V, I, and Y; D, S, V, T, and Y; D, S, I, T, and Y; Four AA subsets: D, S, V, and I; D, S, V, and T; D, S, V, and Y; D, S, I, and T; D, S, I, and Y; D, S, T, and Y; Three AA subsets: D, S, and V; D, S, and I; D, S, and T; D, S, and Y.

Accordingly, formulations (e.g., pharmaceutical formulations) comprising the select six amino acids D, S, V, I, T, Y and subsets thereof comprising three, four, or five amino acid subsets of the select six amino acids and uses thereof for rapidly increasing fluid absorption, as reflected by fluid absorption rate, in a subject in need thereof and/or treating diseases or disorders associated with dehydration, and for use in the preparation of medicaments for treating diseases or disorders associated with dehydration are encompassed herein. The above reasoning is equally applied to any combination of two (D, S), three, four, or five amino acid subsets of the select six amino acids D, S, V, I, T, Y described herein and D, S, V, I, T, Y.

Also encompassed herein are formulations (e.g., pharmaceutical formulations) comprising the select six amino acids D, S, V, I, T, Y and subsets thereof comprising three, four, or five amino acid subsets of the select six amino acids and uses thereof for promoting intestinal barrier function in a subject in need thereof and/or treating diseases or disorders associated with impaired intestinal barrier function, and for use in the preparation of medicaments for treating diseases or disorders associated with impaired intestinal barrier function are encompassed herein. The above reasoning is equally applied to any combination of two (D, S), three, four, or five amino acid subsets of the select six amino acids D, S, V, I, T, Y described herein and D, S, V, I, T, Y.

In some embodiments, the formulation comprises, consists essentially of, or consists of free amino acids of aspartic acid (D) and valine (V) and free amino acids of at least one of serine (S), isoleucine (I), threonine (T) or tyrosine (Y); wherein a concentration of aspartic acid ranges from 14 mM to 30 mM; and wherein a molar ratio of aspartic acid/valine ranges from 3.8 aspartic acid/1 valine to 1.4 aspartic acid/1 valine. The different combinations of this embodiment are presented in List 2 as follows: Six AA: D, V, S, I, T, and Y; Five AA subsets: D, V, S, I, and T; D, V, S, I, and Y; D, V, S, T, and Y; D, V, I, T, and Y; Four AA subsets: D, V, S, and I; D, V, S, and T; D, V, S, and Y; D, V, I, and T; D, V, I, and Y; D, V, T, and Y; and Three AA subsets: D, V, and S; D, V, and I; D, V, and T; D, V, and Y.

Accordingly, formulations (e.g., pharmaceutical formulations) comprising the select six amino acids D, V, S, I, T, Y and subsets thereof comprising three, four, or five amino acid subsets of the select six amino acids and uses thereof for rapidly increasing fluid absorption, as reflected by fluid absorption rate, in a subject in need thereof and/or treating diseases or disorders associated with dehydration, and for use in the preparation of medicaments for treating diseases or disorders associated with dehydration are encompassed herein. The above reasoning is equally applied to any combination of two (D, V), three, four, or five amino acid subsets of the select six amino acids D, V, S, I, T, Y described herein and D, V, S, I, T, Y.

Also encompassed herein are formulations (e.g., pharmaceutical formulations) comprising the select six amino acids D, V, S, I, T, Y and subsets thereof comprising three, four, or five amino acid subsets of the select six amino acids and uses thereof for promoting intestinal barrier function in a subject in need thereof and/or treating diseases or disorders associated with impaired intestinal barrier function, and for use in the preparation of medicaments for treating diseases or disorders associated with impaired intestinal barrier function are encompassed herein. The above reasoning is equally applied to any combination of two (D, V), three, four, or five amino acid subsets of the select six amino acids D, V, S, I, T, Y described herein and D, V, S, I, T, Y.

In some embodiments, the formulation comprises, consists essentially of, or consists of free amino acids of aspartic acid (D), serine (S), and valine (V) and optionally, free amino acids of at least one of isoleucine (I), threonine (T) or tyrosine (Y); wherein a concentration of aspartic acid ranges from 14 mM to 30 mM; and wherein a molar ratio of aspartic acid/serine is ranges from 2.8 aspartic acid/1 serine to 0.9 aspartic acid/1 serine. The different combinations of this embodiment are presented in List 3 as follows: Six AA: D, S, V, I, T, and Y; Five AA subsets: D, S, V, I, and T; D, S, V, I, and Y; D, S, V, T, and Y; and Four AA subsets: D, S, V, and I; D, S, V, and T; D, S, V, and Y.

Accordingly, formulations (e.g., pharmaceutical formulations) comprising the select six amino acids D, S, V, I, T, Y and subsets thereof comprising four or five amino acid subsets of the select six amino acids and uses thereof for rapidly increasing fluid absorption, as reflected by fluid absorption rate, in a subject in need thereof and/or treating diseases or disorders associated with dehydration, and for use in the preparation of medicaments for treating diseases or disorders associated with dehydration are encompassed herein. The above reasoning is equally applied to any combination of three (D, S, V), four, or five amino acid subsets of the select six amino acids D, S, V, I, T, Y described herein and D, S, V, I, T, Y.

Also encompassed herein are formulations (e.g., pharmaceutical formulations) comprising the select six amino acids D, S, V, I, T, Y and subsets thereof comprising four or five amino acid subsets of the select six amino acids and uses thereof for promoting intestinal barrier function in a subject in need thereof and/or treating diseases or disorders associated with impaired intestinal barrier function, and for use in the preparation of medicaments for treating diseases or disorders associated with impaired intestinal barrier function are encompassed herein. The above reasoning is equally applied to any combination of three (D, S, V), four, or five amino acid subsets of the select six amino acids D, S, V, I, T, Y described herein and D, S, V, I, T, Y.

In some embodiments, exemplary formulations described herein comprise: a therapeutically effective combination of free amino acids, wherein the therapeutically effective combination of free amino acids consists essentially of: a therapeutically effective amount of free amino acids of aspartic acid and serine; and a therapeutically effective amount of at least one of free amino acids of valine, isoleucine, threonine, or tyrosine, or any combination thereof; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and serine; and a therapeutically effective amount of at least one of free amino acids of valine, isoleucine, threonine, or tyrosine, or any combination thereof; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and serine; and a therapeutically effective amount of at least one of free amino acids of valine, isoleucine, threonine, or tyrosine, or any combination thereof; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; and optionally, at least one pharmaceutically acceptable carrier, buffer, electrolyte, adjuvant, excipient, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and serine; and a therapeutically effective amount of at least one of free amino acids of valine, isoleucine, threonine, or tyrosine, or any combination thereof; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; and optionally, at least one pharmaceutically acceptable carrier, buffer, electrolyte, adjuvant, excipient, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids comprises, consists essentially of, or consists of a therapeutically effective amount of free amino acids of aspartic acid, serine, and valine; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids comprises, consists essentially of, or consists of a therapeutically effective amount of free amino acids of aspartic acid, serine, and valine; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids comprises, consists essentially of, or consists of a therapeutically effective amount of free amino acids of aspartic acid, serine, and valine; wherein a concentration of aspartic acid ranges from 14 mM to 30 mM; wherein a molar ratio of aspartic acid/serine ranges from 2.8 aspartic acid/1 serine to 0.9 aspartic acid/1 serine; and water; and optionally, at least one pharmaceutically acceptable carrier, buffer, electrolyte, adjuvant, excipient, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids comprises, consists essentially of, or consists of a therapeutically effective amount of free amino acids of aspartic acid, serine, and valine; wherein a concentration of aspartic acid ranges from 14 mM to 30 mM; wherein a molar ratio of aspartic acid/serine ranges from 2.8 aspartic acid/1 serine to 0.9 aspartic acid/1 serine; and water; and optionally, at least one pharmaceutically acceptable carrier, buffer, electrolyte, adjuvant, excipient, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and valine; and a therapeutically effective amount of at least one of free amino acids of serine, isoleucine, threonine, or tyrosine, or any combination thereof; wherein a molar ratio of aspartic acid/valine ranges from 3.8 aspartic acid/1 valine to 1.4 aspartic acid/1 valine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and valine; and a therapeutically effective amount of at least one of free amino acids of serine, isoleucine, threonine, or tyrosine, or any combination thereof; wherein a molar ratio of aspartic acid/valine ranges from 3.8 aspartic acid/1 valine to 1.4 aspartic acid/1 valine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and valine; and a therapeutically effective amount of at least one of free amino acids of serine, isoleucine, threonine, or tyrosine, or any combination thereof; and water; wherein a concentration of aspartic acid ranges from 14 mM to 30 mM; wherein a molar ratio of aspartic acid/valine ranges from 3.8 aspartic acid/1 valine to 1.4 aspartic acid/1 valine; and optionally, at least one pharmaceutically acceptable carrier, buffer, electrolyte, adjuvant, excipient, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of: a therapeutically effective amount of free amino acids of aspartic acid and valine; and a therapeutically effective amount of at least one of free amino acids of serine, isoleucine, threonine, or tyrosine, or any combination thereof; and water; wherein a concentration of aspartic acid ranges from 14 mM to 30 mM; wherein a molar ratio of aspartic acid/valine ranges from 3.8 aspartic acid/1 valine to 1.4 aspartic acid/1 valine; and optionally, at least one pharmaceutically acceptable carrier, buffer, electrolyte, adjuvant, excipient, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; and optionally, at least one pharmaceutically acceptable carrier, buffer, electrolyte, adjuvant, excipient, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; and optionally, at least one pharmaceutically acceptable carrier, buffer, electrolyte, adjuvant, excipient, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine;

wherein a total weight percent of free amino acids of aspartic acid ranges from 30% to 55% of a total weight of the therapeutically effective combination of free amino acids; and optionally, at least one pharmaceutically acceptable carrier, buffer, electrolyte, adjuvant, excipient, or water, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; and water; wherein the concentration of aspartic acid ranges from 14 mM to 30 mM; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; and optionally, at least one pharmaceutically acceptable carrier, buffer, electrolyte, adjuvant, excipient, or any combination thereof; wherein the therapeutically effective combination of free amino acids is sufficient to promote fluid absorption, thereby promoting hydration in the subject. In embodiments thereof, the promoted fluid absorption reflects an increased rate of fluid absorption in the subject, wherein the increased rate is determined relative to the same formulation without free amino acids.

In some embodiments, exemplary formulations described herein comprise: a therapeutically effective combination of free amino acids, wherein the therapeutically effective combination of free amino acids consists essentially of or consists of a therapeutically effective amount of free amino acids of tyrosine, isoleucine, threonine, valine, serine, and aspartic acid; and water; wherein the concentration of aspartic acid ranges from 14 mM to 30 mM; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; and optionally, at least one pharmaceutically acceptable carrier, buffer, electrolyte, adjuvant, excipient, or any combination thereof; wherein the therapeutically effective combination of free amino acids is sufficient to promote intestinal barrier integrity, thereby promoting intestinal barrier function in the subject. In embodiments thereof, the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof in the subject, wherein the increased rate is determined relative to the same formulation without free amino acids.

Control solutions utilized in experimental protocols and for which results are presented herein include: Control (Ringer's saline with 17 mM Na). Ringer's saline with 17 mM NaCl also served as the control solution into which the select 6 amino acids of 6AA-Hyd (aspartic acid, serine, valine, threonine, isoleucine, and tyrosine) or the select 8 amino acids of 8AA (aspartic acid, serine, valine, threonine, isoleucine, tyrosine, lysine, and glycine) were added to generate 6AA-Hyd and 8AA, respectively. 8AA (aspartic acid, serine, valine, threonine, isoleucine, tyrosine, lysine, and glycine) served as a positive comparator solution utilized in experimental protocols. 8AA was used as a positive comparator in studies presented herein because it promotes sodium absorption and fluid uptake.

In some embodiments, a formulation described herein may optionally comprise monosaccharide glucose, at least one glucose-containing disaccharide, or any combination thereof, wherein the total concentration of the monosaccharide glucose, the at least one glucose-containing disaccharide, or any combination thereof is greater than 0 mM and less than 200 mM; is greater than 0 mM and less than 190 mM; is greater than 0 mM and less than 180 mM; is greater than 0 mM and less than 170 mM; is greater than 0 mM and less than 160 mM; is greater than 0 mM and less than 150 mM; is greater than 0 mM and less than 140 mM; is greater than 0 mM and less than 130 mM; is greater than 0 mM and less than 120 mM; is greater than 0 mM and less than 110 mM; is greater than 0 mM and less than 100 mM; or is greater than 0 mM and less than 90 mM. In embodiments thereof, monosaccharide glucose, the at least one glucose-containing disaccharide, or any combination thereof is greater than 0 mM and less than 85 mM; monosaccharide glucose, the at least one glucose-containing disaccharide, or any combination thereof is greater than 0 mM and less than 80 mM; monosaccharide glucose, the at least one glucose-containing disaccharide, or any combination thereof is greater than 0 mM and less than 75 mM; monosaccharide glucose, the at least one glucose-containing disaccharide, or any combination thereof is greater than 0 mM and less than 70 mM; monosaccharide glucose, the at least one glucose-containing disaccharide, or any combination thereof is greater than 0 mM and less than 65 mM; monosaccharide glucose, the at least one glucose-containing disaccharide, or any combination thereof is greater than 0 mM and less than 60 mM; monosaccharide glucose, the at least one glucose-containing disaccharide, or any combination thereof is greater than 0 mM and less than 55 mM; monosaccharide glucose, the at least one glucose-containing disaccharide, or any combination thereof is greater than 0 mM and less than 50 mM; monosaccharide glucose, the at least one glucose-containing disaccharide, or any combination thereof is greater than 0 mM and less than 45 mM; monosaccharide glucose, the at least one glucose-containing disaccharide, or any combination thereof is greater than 0 mM and less than 40 mM; monosaccharide glucose, the at least one glucose-containing disaccharide, or any combination thereof is greater than 0 mM and less than 35 mM; monosaccharide glucose, the at least one glucose-containing disaccharide, or any combination thereof is greater than 0 mM and less than 30 mM; monosaccharide glucose, the at least one glucose-containing disaccharide, or any combination thereof is greater than 0 mM and less than 25 mM; monosaccharide glucose, the at least one glucose-containing disaccharide, or any combination thereof is greater than 0 mM and less than 20 mM; monosaccharide glucose, the at least one glucose-containing disaccharide, or any combination thereof is greater than 0 mM and less than 15 mM; monosaccharide glucose, the at least one glucose-containing disaccharide, or any combination thereof is greater than 0 mM and less than 10 mM; or monosaccharide glucose, the at least one glucose-containing disaccharide, or any combination thereof is greater than 0 mM and less than 5 mM.

In some embodiments thereof, monosaccharide glucose, the at least one glucose-containing disaccharide, or any combination thereof ranges from 10-90 mM; ranges from 10-85 mM; ranges from 10-80 mM; ranges from 10-75 mM; ranges from 10-70 mM; ranges from 10-65 mM; ranges from 10-60 mM; ranges from 10-55 mM; ranges from 10-50 mM; ranges from 10-45 mM; ranges from 10-40 mM; ranges from 10-35 mM; ranges from 10-30 mM; ranges from 10-25 mM; ranges from 10-20 mM; ranges from 5-90 mM; ranges from 5-85 mM; ranges from 5-80 mM; ranges from 5-75 mM; ranges from 5-70 mM; ranges from 5-65 mM; ranges from 5-60 mM; ranges from 5-55 mM; ranges from 5-50 mM; ranges from 5-45 mM; ranges from 5-40 mM; ranges from 5-35 mM; ranges from 5-30 mM; ranges from 5-25 mM; ranges from 5-20 mM; ranges from 1-90 mM; ranges from 1-85 mM; ranges from 1-80 mM; ranges from 1-75 mM; ranges from 1-70 mM; ranges from 1-65 mM; ranges from 1-60 mM; ranges from 1-55 mM; ranges from 1-50 mM; ranges from 1-45 mM; ranges from 1-40 mM; ranges from 1-35 mM; ranges from 1-30 mM; ranges from 1-25 mM; or ranges from 1-20 mM.

In some embodiments, the therapeutic composition does not contain any saccharides, including any mono-, di-, oligo-, polysaccharides, and carbohydrates. In some embodiments, the therapeutic composition does not contain glucose, and/or any di-, oligo, polysaccharides, and carbohydrates that can be hydrolyzed into glucose. In some embodiments, the composition does not contain lactose. In some embodiments, the therapeutic composition does not contain fructose and/or galactose, and/or any di-, oligo, polysaccharides, and carbohydrates that can be hydrolyzed into fructose and/or galactose.

The term "consisting essentially of" as used herein, limits the scope of the ingredients and steps to the specified materials or steps and those that do not materially affect the basic and novel characteristic(s) of the present invention, e.g., formulations or compositions and use thereof for promoting rapid hydration and/or for the treatment of disorders associated with dehydration and methods for treating disorders associated with dehydration. For instance, by using "consisting essentially of" the therapeutic composition does not contain any ingredients not expressly recited in the claims including, but not limited to, free amino acids, di-, oligo, or polypeptides or proteins; and mono-, di-, oligo-, polysaccharides, and carbohydrates that have a direct effect on promoting rapid hydration and/or on treatment of disorders associated with dehydration and methods for treating disorders associated with dehydration. Within the context of "consisting essentially of", a direct effect may be determined based on a rapid change in fluid absorption determined using a single-pass intestinal perfusion assay in rats at 15-90 minutes incubation time, wherein the presence of an ingredient that confers an increase or decrease of up to 1%, 2%, 3%, 4%, or 5% does not materially affect the basic and novel characteristic(s) of formulations or compositions described herein, and thus can fall within the term "consisting essentially of".

Changes in absorption rate of the small bowel can be determined by, for example, using a single-pass intestinal perfusion assay in rats, as illustrated in the Materials and Methods section herein.

In some embodiments, a formulation for use in promoting hydration in a subject in need thereof is envisioned, wherein the formulation comprises: a therapeutically effective combination of free amino acids, wherein the therapeutically effective combination of free amino acids consists essentially of: a therapeutically effective amount of free amino acids of aspartic acid and serine; and a therapeutically effective amount of at least one of free amino acids of valine, isoleucine, threonine, or tyrosine, or any combination thereof; wherein a concentration of aspartic acid ranges from 14 mM to 30 mM; wherein a molar ratio of aspartic acid/tyrosine ranges from 40.0 aspartic acid/1 tyrosine to 9.0 aspartic acid/1 tyrosine; wherein the therapeutically effective combination of free amino acids is sufficient to increase fluid absorption in the subject, as reflected by an increased rate of fluid absorption, thereby promoting hydration in the subject; and wherein the increased rate is determined relative to the same formulation without free amino acids; and optionally, water. In some embodiments of the formulation, the concentration of aspartic acid ranges from 14 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM. In some embodiments of the formulation, the molar ratio of aspartic acid/tyrosine ranges from 40.0 aspartic acid/1 tyrosine to 9.0 aspartic acid/1 tyrosine; the molar ratio of aspartic acid/tyrosine ranges from 36.0 aspartic acid/1 tyrosine to 10.0 aspartic acid/1 tyrosine; the molar ratio of aspartic acid/tyrosine ranges from 36.0 aspartic acid/1 tyrosine to 15.0 aspartic acid/1 tyrosine; the molar ratio of aspartic acid/tyrosine ranges from 36.0 aspartic acid/1 tyrosine to 20.0 aspartic acid/1 tyrosine; the molar ratio of aspartic acid/tyrosine ranges from 24.0 aspartic acid/1 tyrosine to 10.0 aspartic acid/1 tyrosine; the molar ratio of aspartic acid/tyrosine ranges from 24.0 aspartic acid/1 tyrosine to 15.0 aspartic acid/1 tyrosine; the molar ratio of aspartic acid/tyrosine ranges from 24.0 aspartic acid/1 tyrosine to 20.0 aspartic acid/1 tyrosine; the molar ratio of aspartic acid/tyrosine is about 35.8 aspartic acid/1 tyrosine; the molar ratio of aspartic acid/tyrosine is about 23.8 aspartic acid/1 tyrosine; the molar ratio of aspartic acid/tyrosine is about 23.0 aspartic acid/1 tyrosine; the molar ratio of aspartic acid/tyrosine is about 17.5 aspartic acid/1 tyrosine; the molar ratio of aspartic acid/tyrosine is about 15.3 aspartic acid/1 tyrosine; or the molar ratio of aspartic acid/tyrosine is about 11.7 aspartic acid/1 tyrosine.

Some embodiments are listed herein below numerically:

Embodiment 1—A formulation for use in promoting hydration in a subject in need thereof, wherein the formulation comprises: a therapeutically effective combination of free amino acids, wherein the therapeutically effective combination of free amino acids consists essentially of: a therapeutically effective amount of free amino acids of aspartic acid and serine; and a therapeutically effective amount of at least one of free amino acids of valine, isoleucine, threonine, or tyrosine, or any combination thereof; and optionally water; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 2—A formulation for use in promoting hydration in a subject in need thereof, wherein the formulation comprises: a therapeutically effective combination of free amino acids, wherein the therapeutically effective combination of free amino acids consists essentially of: a therapeutically effective amount of free amino acids of aspartic acid and serine; and a therapeutically effective amount of at least one of free amino acids of valine, isoleucine, threonine, or tyrosine, or any combination thereof; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 3—The formulation according to any one of embodiments 1-2, wherein the concentration of aspartic acid ranges from 15 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM.

Embodiment 4—The formulation according to any one of embodiments 1-3, wherein a total weight percent of aspartic acid and serine is greater than a total weight percent of valine, isoleucine, threonine, and tyrosine.

Embodiment 5—The formulation according to any one of embodiments 1-4, wherein the molar ratio of aspartic acid/serine ranges from 2.8 aspartic acid/1 serine to 1 aspartic acid/1 serine; the molar ratio of aspartic acid/serine ranges from 2.7 aspartic acid/1 serine to 1 aspartic acid/1 serine; the molar ratio of aspartic acid/serine ranges from 2.6 aspartic acid/1 serine to 1 aspartic acid/1 serine; the molar ratio of aspartic acid/serine ranges from 2.5 aspartic acid/1 serine to 1 aspartic acid/1 serine; the molar ratio of aspartic acid/serine ranges from 2.4 aspartic acid/1 serine to 1 aspartic acid/1 serine; the molar ratio of aspartic acid/serine ranges from 2.3 aspartic acid/1 serine to 1 aspartic acid/1 serine; the molar ratio of aspartic acid/serine ranges from 2.2 aspartic acid/1 serine to 1 aspartic acid/1 serine; the molar ratio of aspartic acid/serine ranges from 2.1 aspartic acid/1 serine to 1 aspartic acid/1 serine; the molar ratio of aspartic acid/serine ranges from 2.0 aspartic acid/1 serine to 1 aspartic acid/1 serine; the molar ratio of aspartic acid/serine ranges from 1.9 aspartic acid/1 serine to 1 aspartic acid/1 serine; the molar ratio of aspartic acid/serine ranges from 1.8 aspartic acid/1 serine to 1 aspartic acid/1 serine; the molar ratio of aspartic acid/serine ranges from 1.7 aspartic acid/1 serine to 1 aspartic acid/1 serine; the molar ratio of aspartic acid/serine ranges from 1.6 aspartic acid/1 serine to 1 aspartic acid/1 serine; the molar ratio of aspartic acid/serine ranges from 1.5 aspartic acid/1 serine to 1 aspartic acid/1 serine; the molar ratio of aspartic acid/serine ranges from 1.4 aspartic acid/1 serine to 1 aspartic acid/1 serine; the molar ratio of aspartic acid/serine ranges from 1.3 aspartic acid/1 serine to 1 aspartic acid/1 serine; the molar ratio of aspartic acid/serine ranges from 1.2 aspartic acid/1 serine to 1 aspartic acid/1 serine; the molar ratio of aspartic acid/serine ranges from 1.1 aspartic acid/1 serine to 1 aspartic acid/1 serine; the molar ratio is about 2.8 aspartic acid/1 serine; the molar ratio is about 0.9 aspartic acid/1 serine; the molar ratio is about 1.8 aspartic acid/1 serine; or the molar ratio is about 1.2 aspartic acid/1 serine.

Embodiment 6—The formulation according to any one of embodiments 1-5, wherein when valine is present, the molar ratio of aspartic acid/valine ranges from 3.8 aspartic acid/1 valine to 1.4 aspartic acid/1 valine; the molar ratio of aspartic acid/valine ranges from 3.8 aspartic acid/1 valine to 1.5 aspartic acid/1 valine; the molar ratio of aspartic acid/valine ranges from 3.8 aspartic acid/1 valine to 1.6 aspartic acid/1 valine; the molar ratio of aspartic acid/valine ranges from 3.8 aspartic acid/1 valine to 1.7 aspartic acid/1 valine; the molar ratio of aspartic acid/valine ranges from 3.8 aspartic acid/1 valine to 1.8 aspartic acid/1 valine; the molar ratio of aspartic acid/valine ranges from 3.6 aspartic acid/1 valine to 1.4 aspartic acid/1 valine; the molar ratio of aspartic acid/valine ranges from 3.6 aspartic acid/1 valine to 1.5 aspartic acid/1 valine; the molar ratio of aspartic acid/valine ranges from 3.6 aspartic acid/1 valine to 1.6 aspartic acid/1 valine; the molar ratio of aspartic acid/valine ranges from 3.6 aspartic acid/1 valine to 1.7 aspartic acid/1 valine; the molar ratio of aspartic acid/valine ranges from 3.6 aspartic acid/1 valine to 1.8 aspartic acid/1 valine; the molar ratio of aspartic acid/valine ranges from 3.5 aspartic acid/1 valine to 1.8 aspartic acid/1 valine; the molar ratio of aspartic acid/valine ranges from 3.2 aspartic acid/1 valine to 1.9 aspartic acid/1 valine; the molar ratio of aspartic acid/valine ranges from 3.2 aspartic acid/1 valine to 2.0 aspartic acid/1 valine; the molar ratio of aspartic acid/valine ranges from 2.5 aspartic acid/1 valine to 2.0 aspartic acid/1 valine; the molar ratio of aspartic acid/valine ranges from 2.2 aspartic acid/1 valine to 2.0 aspartic acid/1 valine; the molar ratio of aspartic acid/valine ranges from 2.1 aspartic acid/1 valine to 2.0 aspartic acid/1 valine; the molar ratio of aspartic acid/valine is about 3.8 aspartic acid/1 valine; the molar ratio of aspartic acid/valine is about 1.4 aspartic acid/1 valine; the molar ratio of aspartic acid/valine is about 3.2 aspartic acid/1 valine; or the molar ratio of aspartic acid/valine is about 2 aspartic acid/1 valine.

Embodiment 7—The formulation according to any one of embodiments 1-6, wherein when isoleucine is present, the molar ratio of aspartic acid/isoleucine ranges from 5.5 aspartic acid/1 isoleucine to 1.5 aspartic acid/1 isoleucine; the molar ratio of aspartic acid/isoleucine ranges from 5.5 aspartic acid/1 isoleucine to 1.6 aspartic acid/1 isoleucine; the molar ratio of aspartic acid/isoleucine ranges from 5.5 aspartic acid/1 isoleucine to 1.7 aspartic acid/1 isoleucine; the molar ratio of aspartic acid/isoleucine ranges from 5.5 aspartic acid/1 isoleucine to 1.8 aspartic acid/1 isoleucine; the molar ratio of aspartic acid/isoleucine ranges from 5.5 aspartic acid/1 isoleucine to 1.9 aspartic acid/1 isoleucine; the molar ratio of aspartic acid/isoleucine ranges from 5.5 aspartic acid/1 isoleucine to 2.0 aspartic acid/1 isoleucine; the molar ratio of aspartic acid/isoleucine ranges from 5.0 aspartic acid/1 isoleucine to 1.5 aspartic acid/1 isoleucine; the molar ratio of aspartic acid/isoleucine ranges from 5.0 aspartic acid/1 isoleucine to 1.6 aspartic acid/1 isoleucine; the molar ratio of aspartic acid/isoleucine ranges from 5.0 aspartic acid/1 isoleucine to 1.7 aspartic acid/1 isoleucine; the molar ratio of aspartic acid/isoleucine ranges from 5.0 aspartic acid/1 isoleucine to 1.8 aspartic acid/1 isoleucine; the molar ratio of aspartic acid/isoleucine ranges from 5.0 aspartic acid/1 isoleucine to 1.9 aspartic acid/1 isoleucine; the molar ratio of aspartic acid/isoleucine ranges from 5.0 aspartic acid/1 isoleucine to 2.0 aspartic acid/1 isoleucine; the molar ratio of aspartic acid/isoleucine ranges from 4.9 aspartic acid/1 isoleucine to 2.5 aspartic acid/1 isoleucine;

the molar ratio of aspartic acid/isoleucine ranges from 4.8 aspartic acid/1 isoleucine to 2.5 aspartic acid/1 isoleucine; the molar ratio of aspartic acid/isoleucine ranges from 4.7 aspartic acid/1 isoleucine to 2.5 aspartic acid/1 isoleucine; the molar ratio of aspartic acid/isoleucine ranges from 4.6 aspartic acid/1 isoleucine to 2.5 aspartic acid/1 isoleucine; the molar ratio of aspartic acid/isoleucine ranges from 4.5 aspartic acid/1 isoleucine to 2.5 aspartic acid/1 isoleucine; the molar ratio of aspartic acid/isoleucine ranges from 4.4 aspartic acid/1 isoleucine to 2.5 aspartic acid/1 isoleucine; the molar ratio of aspartic acid/isoleucine ranges from 4.4 aspartic acid/1 isoleucine to 2.6 aspartic acid/1 isoleucine; the molar ratio of aspartic acid/isoleucine ranges from 4.4 aspartic acid/1 isoleucine to 2.7 aspartic acid/1 isoleucine; the molar ratio of aspartic acid/isoleucine ranges from 4.4 aspartic acid/1 isoleucine to 2.8 aspartic acid/1 isoleucine; the molar ratio of aspartic acid/isoleucine is about 5.5 aspartic acid/1 isoleucine; the molar ratio of aspartic acid/isoleucine is about 1.5 aspartic acid/1 isoleucine; the molar ratio of aspartic acid/isoleucine is about 4.4 aspartic acid/1 isoleucine; or the molar ratio of aspartic acid/isoleucine is about 2.8 aspartic acid/1 isoleucine.

Embodiment 8—The formulation according to any one of embodiments 1-7, wherein when threonine is present, the molar ratio of aspartic acid/threonine ranges from 5.5 aspartic acid/1 threonine to 1.7 aspartic acid/1 threonine; the molar ratio of aspartic acid/threonine ranges from 5.5 aspartic acid/1 threonine to 1.8 aspartic acid/1 threonine; the molar ratio of aspartic acid/threonine ranges from 5.5 aspartic acid/1 threonine to 1.9 aspartic acid/1 threonine; the molar ratio of aspartic acid/threonine ranges from 5.5 aspartic acid/1 threonine to 2.0 aspartic acid/1 threonine; the molar ratio of aspartic acid/threonine ranges from 5.0 aspartic acid/1 threonine to 1.7 aspartic acid/1 threonine; the molar ratio of aspartic acid/threonine ranges from 5.0 aspartic acid/1 threonine to 1.8 aspartic acid/1 threonine; the molar ratio of aspartic acid/threonine ranges from 5.0 aspartic acid/1 threonine to 1.9 aspartic acid/1 threonine; the molar ratio of aspartic acid/threonine ranges from 5.0 aspartic acid/1 threonine to 2.0 aspartic acid/1 threonine; the molar ratio of aspartic acid/threonine ranges from 4.9 aspartic acid/1 threonine to 2.5 aspartic acid/1 threonine; the molar ratio of aspartic acid/threonine ranges from 4.8 aspartic acid/1 threonine to 2.5 aspartic acid/1 threonine; the molar ratio of aspartic acid/threonine ranges from 4.7 aspartic acid/1 threonine to 2.5 aspartic acid/1 threonine; the molar ratio of aspartic acid/threonine ranges from 4.6 aspartic acid/1 threonine to 2.5 aspartic acid/1 threonine; the molar ratio of aspartic acid/threonine ranges from 4.5 aspartic acid/1 threonine to 2.5 aspartic acid/1 threonine; the molar ratio of aspartic acid/threonine ranges from 4.4 aspartic acid/1 threonine to 2.5 aspartic acid/1 threonine; the molar ratio of aspartic acid/threonine ranges from 4.4 aspartic acid/1 threonine to 2.6 aspartic acid/1 threonine; the molar ratio of aspartic acid/threonine ranges from 4.4 aspartic acid/1 threonine to 2.7 aspartic acid/1 threonine; the molar ratio of aspartic acid/threonine ranges from 4.4 aspartic acid/1 threonine to 2.8 aspartic acid/1 threonine; the molar ratio of aspartic acid/threonine is about 5.5 aspartic acid/1 threonine; the molar ratio of aspartic acid/threonine is about 1.7 aspartic acid/1 threonine; the molar ratio of aspartic acid/threonine is about 4.4 aspartic acid/1 threonine; or the molar ratio of aspartic acid/threonine is about 2.8 aspartic acid/1 threonine.

Embodiment 9—The formulation according to any one of embodiments 1-8, wherein when tyrosine is present, the molar ratio of aspartic acid/tyrosine ranges from 40.0 aspartic acid/1 tyrosine to 9.0 aspartic acid/1 tyrosine; the molar ratio of aspartic acid/tyrosine ranges from 36.0 aspartic acid/1 tyrosine to 10.0 aspartic acid/1 tyrosine; the molar ratio of aspartic acid/tyrosine ranges from 36.0 aspartic acid/1 tyrosine to 15.0 aspartic acid/1 tyrosine; the molar ratio of aspartic acid/tyrosine ranges from 36.0 aspartic acid/1 tyrosine to 20.0 aspartic acid/1 tyrosine; the molar ratio of aspartic acid/tyrosine ranges from 24.0 aspartic acid/1 tyrosine to 10.0 aspartic acid/1 tyrosine; the molar ratio of aspartic acid/tyrosine ranges from 24.0 aspartic acid/1 tyrosine to 15.0 aspartic acid/1 tyrosine; the molar ratio of aspartic acid/tyrosine ranges from 24.0 aspartic acid/1 tyrosine to 20.0 aspartic acid/1 tyrosine; the molar ratio of aspartic acid/tyrosine is about 35.8 aspartic acid/1 tyrosine; the molar ratio of aspartic acid/tyrosine is about 23.8 aspartic acid/1 tyrosine; the molar ratio of aspartic acid/tyrosine is about 23.0 aspartic acid/1 tyrosine; the molar ratio of aspartic acid/tyrosine is about 17.5 aspartic acid/1 tyrosine; the molar ratio of aspartic acid/tyrosine is about 15.3 aspartic acid/1 tyrosine; or the molar ratio of aspartic acid/tyrosine is about 11.7 aspartic acid/1 tyrosine.

Embodiment 10—The formulation according to any one of embodiments 1-9, wherein the therapeutically effective combination of free amino acids consists essentially of a therapeutically effective amount of free amino acids of aspartic acid, serine, and valine.

Embodiment 11—The formulation according to any one of embodiments 1-9, wherein the therapeutically effective combination of free amino acids consists essentially of a therapeutically effective amount of free amino acids of aspartic acid, serine, and valine, and optionally, at least one of free amino acids of isoleucine, threonine, or tyrosine, or any combination thereof.

Embodiment 12—The formulation according to any one of embodiments 1-9 or 11, wherein the therapeutically effective combination of free amino acids consists essentially of a therapeutically effective amount of free amino acids of aspartic acid, serine, valine, and isoleucine; or consists essentially of a therapeutically effective amount of free amino acids of aspartic acid, serine, valine, and threonine; and optionally, free amino acids of tyrosine.

Embodiment 13—The formulation according to any one of embodiments 1-9, or 11, wherein the therapeutically effective combination of free amino acids consists essentially of a therapeutically effective amount of free amino acids of aspartic acid, serine, valine, isoleucine, threonine, and tyrosine.

Embodiment 14—The formulation according to any one of embodiments 1-9, wherein the therapeutically effective combination of free amino acids consists essentially of a therapeutically effective amount of free amino acids of: aspartic acid, serine, and isoleucine; and optionally, at least one of free amino acids of threonine or tyrosine, or any combination thereof; aspartic acid, serine, and threonine; and optionally, free amino acids of tyrosine; aspartic acid, serine, valine, and isoleucine; and optionally, at least one of free amino acids of threonine or tyrosine, or any combination thereof; aspartic acid, serine, valine, and threonine; and optionally, free amino acids of tyrosine; aspartic acid, serine, and tyrosine; or aspartic acid, serine, valine, and tyrosine.

Embodiment 15—A formulation for use in promoting hydration in a subject in need thereof, wherein the formulation comprises: a therapeutically effective combination of free amino acids, wherein the therapeutically effective combination of free amino acids comprises or consists essentially of a therapeutically effective amount of free amino acids of aspartic acid, serine, and valine; and optionally water; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 16—A formulation for use in promoting hydration in a subject in need thereof, wherein the formulation comprises: a therapeutically effective combination of free amino acids, wherein the therapeutically effective combination of free amino acids comprises or consists essentially of a therapeutically effective amount of free amino acids of aspartic acid, serine, and valine; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 17—the formulation according any one of embodiments 15-16, wherein the concentration of aspartic acid ranges from 15 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM.

Embodiment 18—the formulation according to any one of embodiments 15-17, wherein the molar ratio of aspartic acid/serine ranges from 2.8 aspartic acid/1 serine to 1 aspartic acid/1 serine; the molar ratio of aspartic acid/serine ranges from 2.7 aspartic acid/1 serine to 1 aspartic acid/1 serine; the molar ratio of aspartic acid/serine ranges from 2.6 aspartic acid/1 serine to 1 aspartic acid/1 serine; the molar ratio of aspartic acid/serine ranges from 2.5 aspartic acid/1 serine to 1 aspartic acid/1 serine; the molar ratio of aspartic acid/serine ranges from 2.4 aspartic acid/1 serine to 1 aspartic acid/1 serine; the molar ratio of aspartic acid/serine ranges from 2.3 aspartic acid/1 serine to 1 aspartic acid/1 serine; the molar ratio of aspartic acid/serine ranges from 2.2 aspartic acid/1 serine to 1 aspartic acid/1 serine; the molar ratio of aspartic acid/serine ranges from 2.1 aspartic acid/1 serine to 1 aspartic acid/1 serine; the molar ratio of aspartic acid/serine ranges from 2.0 aspartic acid/1 serine to 1 aspartic acid/1 serine; the molar ratio of aspartic acid/serine ranges from 1.9 aspartic acid/1 serine to 1 aspartic acid/1 serine; the molar ratio of aspartic acid/serine ranges from 1.8 aspartic acid/1 serine to 1 aspartic acid/1 serine; the molar ratio of aspartic acid/serine ranges from 1.7 aspartic acid/1 serine to 1 aspartic acid/1 serine; the molar ratio of aspartic acid/serine ranges from 1.6 aspartic acid/1 serine to 1 aspartic acid/1 serine; the molar ratio of aspartic acid/serine ranges from 1.5 aspartic acid/1 serine to 1 aspartic acid/1 serine; the molar ratio of aspartic acid/serine ranges from 1.4 aspartic acid/1 serine to 1 aspartic acid/1 serine; the molar ratio of aspartic acid/serine ranges from 1.3 aspartic acid/1 serine to 1 aspartic acid/1 serine; the molar ratio of aspartic acid/serine ranges from 1.2 aspartic acid/1 serine to 1 aspartic acid/1 serine; the molar ratio of aspartic acid/serine ranges from 1.1 aspartic acid/1 serine to 1 aspartic acid/1 serine; the molar ratio is about 2.8 aspartic acid/1 serine; the molar ratio is about 0.9 aspartic acid/1 serine; the molar ratio is about 1.8 aspartic acid/1 serine; or the molar ratio is about 1.2 aspartic acid/1 serine.

Embodiment 19—the formulation according to any one of embodiments 15-18, wherein the molar ratio of aspartic acid/valine ranges from 3.8 aspartic acid/1 valine to 1.4 aspartic acid/1 valine; the molar ratio of aspartic acid/valine ranges from 3.8 aspartic acid/1 valine to 1.5 aspartic acid/1 valine; the molar ratio of aspartic acid/valine ranges from 3.8 aspartic acid/1 valine to 1.6 aspartic acid/1 valine; the molar ratio of aspartic acid/valine ranges from 3.8 aspartic acid/1 valine to 1.7 aspartic acid/1 valine; the molar ratio of aspartic acid/valine ranges from 3.8 aspartic acid/1 valine to 1.8 aspartic acid/1 valine; the molar ratio of aspartic acid/valine ranges from 3.6 aspartic acid/1 valine to 1.4 aspartic acid/1 valine; wherein the molar ratio of aspartic acid/valine ranges from 3.6 aspartic acid/1 valine to 1.5 aspartic acid/1 valine; the molar ratio of aspartic acid/valine ranges from 3.6 aspartic acid/1 valine to 1.6 aspartic acid/1 valine; the molar ratio of aspartic acid/valine ranges from 3.6 aspartic acid/1 valine to 1.7 aspartic acid/1 valine; the molar ratio of aspartic acid/valine ranges from 3.6 aspartic acid/1 valine to 1.8 aspartic acid/1 valine; the molar ratio of aspartic acid/valine ranges from 3.5 aspartic acid/1 valine to 1.8 aspartic acid/1 valine; the molar ratio of aspartic acid/valine ranges from 3.2 aspartic acid/1 valine to 1.9 aspartic acid/1 valine; the molar ratio of aspartic acid/valine ranges from 3.2 aspartic acid/1 valine to 2.0 aspartic acid/1 valine; the molar ratio of aspartic acid/valine ranges from 2.5 aspartic acid/1 valine to 2.0 aspartic acid/1 valine; the molar ratio of aspartic acid/valine ranges from 2.2 aspartic acid/1 valine to 2.0 aspartic acid/1 valine; the molar ratio of aspartic acid/valine ranges from 2.1 aspartic acid/1 valine to 2.0 aspartic acid/1 valine; the molar ratio of aspartic acid/valine is about 3.8 aspartic acid/1 valine; the molar ratio of aspartic acid/valine is about 1.4 aspartic acid/1 valine; the molar ratio of aspartic acid/valine is about 3.2 aspartic acid/1 valine; or the molar ratio of aspartic acid/valine is about 2 aspartic acid/1 valine.

Embodiment 20—the formulation according to any one of embodiments 15-19, wherein the therapeutically effective combination of free amino acids consists essentially of a therapeutically effective amount of free amino acids of aspartic acid, serine, and valine.

Embodiment 21—A formulation for use in promoting hydration in a subject in need thereof, wherein the formulation comprises: a therapeutically effective combination of free amino acids, wherein the therapeutically effective combination of free amino acids consists essentially of: a therapeutically effective amount of free amino acids of aspartic acid and valine; and a therapeutically effective amount of at least one of free amino acids of serine, isoleucine, threonine, or tyrosine, or any combination thereof; and optionally water; wherein a molar ratio of aspartic acid/valine ranges from 3.8 aspartic acid/1 valine to 1.4 aspartic acid/1 valine; wherein a total weight percent of free amino acids of aspartic acid ranges from 30% to 55% of a total weight of the therapeutically effective combination of free amino acids; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 22—A formulation for use in promoting hydration in a subject in need thereof, wherein the formulation comprises: a therapeutically effective combination of free amino acids, wherein the therapeutically effective combination of free amino acids consists essentially of: a therapeutically effective amount of free amino acids of aspartic acid and valine; and a therapeutically effective amount of at least one of free amino acids of serine, isoleucine, threonine, or tyrosine, or any combination thereof; and water; wherein a concentration of aspartic acid ranges from 14 mM to 30 mM; wherein a molar ratio of aspartic acid/valine ranges from 3.8 aspartic acid/1 valine to 1.4 aspartic acid/1 valine; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 23—the formulation according to any one of embodiments 21-22, wherein the concentration of aspartic acid ranges from 15 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM.

Embodiment 24—the formulation according to any one of embodiments 21-23, wherein the molar ratio of aspartic acid/valine ranges from 3.8 aspartic acid/1 valine to 1.4 aspartic acid/1 valine; the molar ratio of aspartic acid/valine ranges from 3.8 aspartic acid/1 valine to 1.5 aspartic acid/1 valine; the molar ratio of aspartic acid/valine ranges from 3.8 aspartic acid/1 valine to 1.6 aspartic acid/1 valine; the molar ratio of aspartic acid/valine ranges from 3.8 aspartic acid/1 valine to 1.7 aspartic acid/1 valine; the molar ratio of aspartic acid/valine ranges from 3.8 aspartic acid/1 valine to 1.8 aspartic acid/1 valine; the molar ratio of aspartic acid/valine ranges from 3.6 aspartic acid/1 valine to 1.4 aspartic acid/1 valine; the molar ratio of aspartic acid/valine ranges from 3.6 aspartic acid/1 valine to 1.5 aspartic acid/1 valine; the molar ratio of aspartic acid/valine ranges from 3.6 aspartic acid/1 valine to 1.6 aspartic acid/1 valine; the molar ratio of aspartic acid/valine ranges from 3.6 aspartic acid/1 valine to 1.7 aspartic acid/1 valine;

the molar ratio of aspartic acid/valine ranges from 3.6 aspartic acid/1 valine to 1.8 aspartic acid/1 valine; the molar ratio of aspartic acid/valine ranges from 3.5 aspartic acid/1 valine to 1.8 aspartic acid/1 valine; the molar ratio of aspartic acid/valine ranges from 3.2 aspartic acid/1 valine to 1.9 aspartic acid/1 valine; the molar ratio of aspartic acid/valine ranges from 3.2 aspartic acid/1 valine to 2.0 aspartic acid/1 valine; the molar ratio of aspartic acid/valine ranges from 2.5 aspartic acid/1 valine to 2.0 aspartic acid/1 valine; the molar ratio of aspartic acid/valine ranges from 2.2 aspartic acid/1 valine to 2.0 aspartic acid/1 valine; the molar ratio of aspartic acid/valine ranges from 2.1 aspartic acid/1 valine to 2.0 aspartic acid/1 valine; the molar ratio of aspartic acid/valine is about 3.8 aspartic acid/1 valine; the molar ratio of aspartic acid/valine is about 1.4 aspartic acid/1 valine; the molar ratio of aspartic acid/valine is about 3.2 aspartic acid/1 valine; or the molar ratio of aspartic acid/1 valine is about 2 aspartic acid/1 valine.

Embodiment 25—the formulation according to any one of embodiments 21-24, wherein when serine is present, the molar ratio of aspartic acid/serine ranges from 2.8 aspartic acid/1 serine to 1 aspartic acid/1 serine; the molar ratio of aspartic acid/serine ranges from 2.7 aspartic acid/1 serine to 1 aspartic acid/1 serine; the molar ratio of aspartic acid/ serine ranges from 2.6 aspartic acid/1 serine to 1 aspartic acid/1 serine; the molar ratio of aspartic acid/serine ranges from 2.5 aspartic acid/1 serine to 1 aspartic acid/1 serine; the molar ratio of aspartic acid/serine ranges from 2.4 aspartic acid/1 serine to 1 aspartic acid/1 serine; the molar ratio of aspartic acid/serine ranges from 2.3 aspartic acid/1 serine to 1 aspartic acid/1 serine; the molar ratio of aspartic acid/ serine ranges from 2.2 aspartic acid/1 serine to 1 aspartic acid/1 serine; the molar ratio of aspartic acid/serine ranges from 2.1 aspartic acid/1 serine to 1 aspartic acid/1 serine; the molar ratio of aspartic acid/serine ranges from 2.0 aspartic acid/1 serine to 1 aspartic acid/1 serine; the molar ratio of aspartic acid/serine ranges from 1.9 aspartic acid/1 serine to 1 aspartic acid/1 serine; the molar ratio of aspartic acid/ serine ranges from 1.8 aspartic acid/1 serine to 1 aspartic acid/1 serine; the molar ratio of aspartic acid/serine ranges from 1.7 aspartic acid/1 serine to 1 aspartic acid/1 serine; the molar ratio of aspartic acid/serine ranges from 1.6 aspartic acid/1 serine to 1 aspartic acid/1 serine; the molar ratio of aspartic acid/serine ranges from 1.5 aspartic acid/1 serine to 1 aspartic acid/1 serine; the molar ratio of aspartic acid/ serine ranges from 1.4 aspartic acid/1 serine to 1 aspartic acid/1 serine; the molar ratio of aspartic acid/serine ranges from 1.3 aspartic acid/1 serine to 1 aspartic acid/1 serine; the molar ratio of aspartic acid/serine ranges from 1.2 aspartic acid/1 serine to 1 aspartic acid/1 serine; the molar ratio of aspartic acid/serine ranges from 1.1 aspartic acid/1 serine to 1 aspartic acid/1 serine; the molar ratio is about 2.8 aspartic acid/1 serine; the molar ratio is about 0.9 aspartic acid/1 serine; the molar ratio is about 1.8 aspartic acid/1 serine; or the molar ratio is about 1.2 aspartic acid/1 serine.

Embodiment 26—the formulation according to any one of embodiments 21-25, wherein when isoleucine is present, the molar ratio of aspartic acid/isoleucine ranges from 5.5 aspartic acid/1 isoleucine to 1.5 aspartic acid/1 isoleucine; the molar ratio of aspartic acid/isoleucine ranges from 5.5 aspartic acid/1 isoleucine to 1.6 aspartic acid/1 isoleucine; the molar ratio of aspartic acid/isoleucine ranges from 5.5 aspartic acid/1 isoleucine to 1.7 aspartic acid/1 isoleucine; the molar ratio of aspartic acid/isoleucine ranges from 5.5 aspartic acid/1 isoleucine to 1.8 aspartic acid/1 isoleucine; the molar ratio of aspartic acid/isoleucine ranges from 5.5 aspartic acid/1 isoleucine to 1.9 aspartic acid/1 isoleucine; the molar ratio of aspartic acid/isoleucine ranges from 5.5 aspartic acid/1 isoleucine to 2.0 aspartic acid/1 isoleucine; the molar ratio of aspartic acid/isoleucine ranges from 5.0 aspartic acid/1 isoleucine to 1.5 aspartic acid/1 isoleucine; the molar ratio of aspartic acid/isoleucine ranges from 5.0 aspartic acid/1 isoleucine to 1.6 aspartic acid/1 isoleucine; the molar ratio of aspartic acid/isoleucine ranges from 5.0 aspartic acid/1 isoleucine to 1.7 aspartic acid/1 isoleucine; the molar ratio of aspartic acid/isoleucine ranges from 5.0 aspartic acid/1 isoleucine to 1.8 aspartic acid/1 isoleucine; the molar ratio of aspartic acid/isoleucine ranges from 5.0 aspartic acid/1 isoleucine to 1.9 aspartic acid/1 isoleucine; the molar ratio of aspartic acid/isoleucine ranges from 5.0 aspartic acid/1 isoleucine to 2.0 aspartic acid/1 isoleucine; the molar ratio of aspartic acid/isoleucine ranges from 4.9 aspartic acid/1 isoleucine to 2.5 aspartic acid/1 isoleucine; the molar ratio of aspartic acid/isoleucine ranges from 4.8 aspartic acid/1 isoleucine to 2.5 aspartic acid/1 isoleucine; the molar ratio of aspartic acid/isoleucine ranges from 4.7 aspartic acid/1 isoleucine to 2.5 aspartic acid/1 isoleucine; the molar ratio of aspartic acid/isoleucine ranges from 4.6 aspartic acid/1 isoleucine to 2.5 aspartic acid/1 isoleucine; the molar ratio of aspartic acid/isoleucine ranges from 4.5 aspartic acid/1 isoleucine to 2.5 aspartic acid/1 isoleucine;

the molar ratio of aspartic acid/isoleucine ranges from 4.4 aspartic acid/1 isoleucine to 2.5 aspartic acid/1 isoleucine; the molar ratio of aspartic acid/isoleucine ranges from 4.4 aspartic acid/1 isoleucine to 2.6 aspartic acid/1 isoleucine; the molar ratio of aspartic acid/isoleucine ranges from 4.4 aspartic acid/1 isoleucine to 2.7 aspartic acid/1 isoleucine; the molar ratio of aspartic acid/isoleucine ranges from 4.4 aspartic acid/1 isoleucine to 2.8 aspartic acid/1 isoleucine; the molar ratio of aspartic acid/isoleucine is about 5.5 aspartic acid/1 isoleucine; the molar ratio of aspartic acid/isoleucine is about 1.5 aspartic acid/1 isoleucine; the molar ratio of aspartic acid/isoleucine is about 4.4 aspartic acid/1 isoleucine; or the molar ratio of aspartic acid/isoleucine is about 2.8 aspartic acid/1 isoleucine.

Embodiment 27—the formulation according to any one of embodiments 21-26, wherein when threonine is present, the molar ratio of aspartic acid/threonine ranges from 5.5 aspartic acid/1 threonine to 1.7 aspartic acid/1 threonine; the molar ratio of aspartic acid/threonine ranges from 5.5 aspartic acid/1 threonine to 1.8 aspartic acid/1 threonine; the molar ratio of aspartic acid/threonine ranges from 5.5 aspartic acid/1 threonine to 1.9 aspartic acid/1 threonine; the molar ratio of aspartic acid/threonine ranges from 5.5 aspartic acid/1 threonine to 2.0 aspartic acid/1 threonine; the molar ratio of aspartic acid/threonine ranges from 5.0 aspartic acid/1 threonine to 1.7 aspartic acid/1 threonine; the molar ratio of aspartic acid/threonine ranges from 5.0 aspartic acid/1 threonine to 1.8 aspartic acid/1 threonine; the molar ratio of aspartic acid/threonine ranges from 5.0 aspartic acid/1 threonine to 1.9 aspartic acid/1 threonine; the molar ratio of aspartic acid/threonine ranges from 5.0 aspartic acid/1 threonine to 2.0 aspartic acid/1 threonine; the molar ratio of aspartic acid/threonine ranges from 4.9 aspartic acid/1 threonine to 2.5 aspartic acid/1 threonine; the molar ratio of aspartic acid/threonine ranges from 4.8 aspartic acid/1 threonine to 2.5 aspartic acid/1 threonine; the molar ratio of aspartic acid/threonine ranges from 4.7 aspartic acid/1 threonine to 2.5 aspartic acid/1 threonine; the molar ratio of aspartic acid/threonine ranges from 4.6 aspartic acid/1 threonine to 2.5 aspartic acid/1 threonine; the molar ratio of aspartic acid/threonine ranges from 4.5 aspartic acid/1 threonine to 2.5 aspartic acid/1 threonine; the molar ratio of aspartic acid/threonine ranges from 4.4 aspartic acid/1 threonine to 2.5 aspartic acid/1 threonine; the molar ratio of aspartic acid/threonine ranges from 4.4 aspartic acid/1 threonine to 2.6 aspartic acid/1 threonine; the molar ratio of aspartic acid/threonine ranges from 4.4 aspartic acid/1 threonine to 2.7 aspartic acid/1 threonine; the molar ratio of aspartic acid/threonine ranges from 4.4 aspartic acid/1 threonine to 2.8 aspartic acid/1 threonine; the molar ratio of aspartic acid/threonine is about 5.5 aspartic acid/1 threonine; the molar ratio of aspartic acid/threonine is about 1.7 aspartic acid/1 threonine; the molar ratio of aspartic acid/threonine is about 4.4 aspartic acid/1 threonine; or the molar ratio of aspartic acid/threonine is about 2.8 aspartic acid/1 threonine.

Embodiment 28—the formulation according to any one of embodiments 21-27, wherein when tyrosine is present, the molar ratio of aspartic acid/tyrosine ranges from 40.0 aspartic acid/1 tyrosine to 9.0 aspartic acid/1 tyrosine; the molar ratio of aspartic acid/tyrosine ranges from 36.0 aspartic acid/1 tyrosine to 10.0 aspartic acid/1 tyrosine; the molar ratio of aspartic acid/tyrosine ranges from 36.0 aspartic acid/1 tyrosine to 15.0 aspartic acid/1 tyrosine; the molar ratio of aspartic acid/tyrosine ranges from 36.0 aspartic acid/1 tyrosine to 20.0 aspartic acid/1 tyrosine; the molar ratio of aspartic acid/tyrosine ranges from 24.0 aspartic acid/1 tyrosine to 10.0 aspartic acid/1 tyrosine; the molar ratio of aspartic acid/tyrosine ranges from 24.0 aspartic acid/1 tyrosine to 15.0 aspartic acid/1 tyrosine; the molar ratio of aspartic acid/tyrosine ranges from 24.0 aspartic acid/1 tyrosine to 20.0 aspartic acid/1 tyrosine; the molar ratio of aspartic acid/tyrosine is about 35.8 aspartic acid/1 tyrosine; the molar ratio of aspartic acid/tyrosine is about 23.8 aspartic acid/1 tyrosine; the molar ratio of aspartic acid/tyrosine is about 23.0 aspartic acid/1 tyrosine; the molar ratio of aspartic acid/tyrosine is about 17.5 aspartic acid/1 tyrosine; the molar ratio of aspartic acid/tyrosine is about 15.3 aspartic acid/1 tyrosine; or the molar ratio of aspartic acid/tyrosine is about 11.7 aspartic acid/1 tyrosine.

Embodiment 29—the formulation according to any one of embodiments 21-28, wherein the therapeutically effective combination of free amino acids consists essentially of a therapeutically effective amount of free amino acids of aspartic acid, valine, and serine.

Embodiment 30—the formulation according to any one of embodiments 21-28, wherein the therapeutically effective combination of free amino acids consists essentially of a therapeutically effective amount of free amino acids of aspartic acid, valine, and serine, and optionally, at least one of free amino acids of isoleucine, threonine, or tyrosine, or any combination thereof.

Embodiment 31—the formulation according to any one of embodiments 21-28 or 30, wherein the therapeutically effective combination of free amino acids consists essentially of a therapeutically effective amount of free amino acids of aspartic acid, valine, serine, and isoleucine; or consists essentially of a therapeutically effective amount of free amino acids of aspartic acid, valine, serine, and threonine; and optionally, free amino acid of tyrosine.

Embodiment 32—the formulation according to any one of embodiments 21-28, wherein the therapeutically effective combination of free amino acids consists essentially of a therapeutically effective amount of free amino acids of aspartic acid, valine, serine, and threonine, and optionally, at least one of free amino acids of isoleucine or tyrosine, or any combination thereof.

Embodiment 33—the formulation according to any one of embodiments 21-28, wherein the therapeutically effective combination of free amino acids consists essentially of a therapeutically effective amount of free amino acids of aspartic acid, valine, serine, isoleucine, and threonine, and optionally, free amino acid of tyrosine.

Embodiment 34—the formulation according to any one of embodiments 21-28, wherein the therapeutically effective combination of free amino acids consists essentially of a therapeutically effective amount of free amino acids of: aspartic acid, valine, and isoleucine; and optionally, at least one of free amino acids of threonine or tyrosine, or any combination thereof; aspartic acid, valine, and threonine; and optionally, free amino acids of tyrosine; or aspartic acid, serine, valine, and tyrosine.

Embodiment 35—the formulation according to any one of embodiments 21-28, wherein the therapeutically effective combination of free amino acids consists essentially of a therapeutically effective amount of aspartic acid, valine, serine, isoleucine, threonine, and tyrosine.

Embodiment 36—A formulation for use in promoting hydration in a subject in need thereof, wherein the formulation comprises: a therapeutically effective combination of free amino acids, wherein the therapeutically effective combination of free amino acids consists essentially of a therapeutically effective amount of free amino acids of tyrosine, isoleucine, threonine, valine, serine, and aspartic acid; and optionally water; wherein a molar ratio of aspartic acid/serine ranges from 2.8 aspartic acid/1 serine to 0.9 aspartic acid/1 serine; wherein a total weight percent of free amino acids of aspartic acid ranges from 30% to 55% of a total weight of the therapeutically effective combination of free amino acids; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 37—A formulation for use in promoting hydration in a subject in need thereof, wherein the formulation comprises: a therapeutically effective combination of free amino acids, wherein the therapeutically effective combination of free amino acids consists essentially of a therapeutically effective amount of free amino acids of tyrosine, isoleucine, threonine, valine, serine, and aspartic acid; and water; wherein a concentration of aspartic acid ranges from 14 mM to 30 mM; wherein a molar ratio of aspartic acid/serine ranges from 2.8 aspartic acid/1 serine to 0.9 aspartic acid/1 serine; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 38—A formulation for use in promoting hydration in a subject in need thereof, wherein the formulation comprises: a therapeutically effective combination of free amino acids, wherein the therapeutically effective combination of free amino acids consists essentially of a therapeutically effective amount of free amino acids of tyrosine, isoleucine, threonine, valine, serine, and aspartic acid; and optionally water; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; wherein a total weight percent of free amino acids of aspartic acid ranges from 30% to 55% of a total weight of the therapeutically effective combination of free amino acids; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 39—A formulation for use in promoting hydration in a subject in need thereof, wherein the formulation comprises: a therapeutically effective combination of free amino acids, wherein the therapeutically effective combination of free amino acids consists essentially of a therapeutically effective amount of free amino acids of tyrosine, isoleucine, threonine, valine, serine, and aspartic acid; and water; wherein the concentration of aspartic acid ranges from 14 mM to 30 mM; wherein a molar ratio of aspartic acid/serine ranges from 2.8 aspartic acid/1 serine to 0.9 aspartic acid/1 serine; wherein a molar ratio of aspartic acid/valine ranges from 3.8 aspartic acid/1 valine to 1.4 aspartic acid/1 valine; wherein the therapeutically effective combination of free amino acids is sufficient to increase rate of fluid absorption in the subject, thereby promoting hydration in the subject; and wherein the increased rate is determined relative to the same formulation without free amino acids.

Embodiment 40—The formulation according to any one of embodiments 36-39, wherein the concentration of aspartic acid ranges from 15 mM to 20 mM; the concentration of aspartic acid ranges from 17 mM to 20 mM; the concentration of aspartic acid ranges from 18 mM to 19 mM; the concentration of aspartic acid ranges from 20 mM to 30 mM; the concentration of aspartic acid ranges from 25 mM to 30 mM; the concentration of aspartic acid ranges from 27 mM to 30 mM; or the concentration of aspartic acid ranges from 28 mM to 29 mM.

Embodiment 41—The formulation according to any one of embodiments 36-40, wherein the molar ratio of aspartic acid/serine ranges from 2.8 aspartic acid/1 serine to 1 aspartic acid/1 serine; the molar ratio of aspartic acid/serine ranges from 2.7 aspartic acid/1 serine to 1 aspartic acid/1 serine; the molar ratio of aspartic acid/serine ranges from 2.6 aspartic acid/1 serine to 1 aspartic acid/1 serine; the molar ratio of aspartic acid/serine ranges from 2.5 aspartic acid/1 serine to 1 aspartic acid/1 serine; the molar ratio of aspartic acid/serine ranges from 2.4 aspartic acid/1 serine to 1 aspartic acid/1 serine; the molar ratio of aspartic acid/serine ranges from 2.3 aspartic acid/1 serine to 1 aspartic acid/1 serine; the molar ratio of aspartic acid/serine ranges from 2.2 aspartic acid/1 serine to 1 aspartic acid/1 serine; the molar ratio of aspartic acid/serine ranges from 2.1 aspartic acid/1 serine to 1 aspartic acid/1 serine; the molar ratio of aspartic acid/serine ranges from 2.0 aspartic acid/1 serine to 1 aspartic acid/1 serine; the molar ratio of aspartic acid/serine ranges from 1.9 aspartic acid/1 serine to 1 aspartic acid/1 serine; the molar ratio of aspartic acid/serine ranges from 1.8 aspartic acid/1 serine to 1 aspartic acid/1 serine; the molar ratio of aspartic acid/serine ranges from 1.7 aspartic acid/1 serine to 1 aspartic acid/1 serine; the molar ratio of aspartic acid/serine ranges from 1.6 aspartic acid/1 serine to 1 aspartic acid/1 serine; the molar ratio of aspartic acid/serine ranges from 1.5 aspartic acid/1 serine to 1 aspartic acid/1 serine; the molar ratio of aspartic acid/serine ranges from 1.4 aspartic acid/1 serine to 1 aspartic acid/1 serine; the molar ratio of aspartic acid/serine ranges from 1.3 aspartic acid/1 serine to 1 aspartic acid/1 serine; the molar ratio of aspartic acid/serine ranges from 1.2 aspartic acid/1 serine to 1 aspartic acid/1 serine; the molar ratio of aspartic acid/serine ranges from 1.1 aspartic acid/1 serine to 1 aspartic acid/1 serine; the molar ratio is about 2.8 aspartic acid/1 serine; the molar ratio is about 0.9 aspartic acid/1 serine; the molar ratio is about 1.8 aspartic acid/1 serine; or the molar ratio is about 1.2 aspartic acid/1 serine.

Embodiment 42—The formulation according to any one of embodiments 36-41, wherein the molar ratio of aspartic acid/valine ranges from 3.8 aspartic acid/1 valine to 1.4 aspartic acid/1 valine; the molar ratio of aspartic acid/valine ranges from 3.8 aspartic acid/1 valine to 1.5 aspartic acid/1 valine; the molar ratio of aspartic acid/valine ranges from 3.8 aspartic acid/1 valine to 1.6 aspartic acid/1 valine; the molar ratio of aspartic acid/valine ranges from 3.8 aspartic acid/1 valine to 1.7 aspartic acid/1 valine; the molar ratio of aspartic acid/valine ranges from 3.8 aspartic acid/1 valine to 1.8 aspartic acid/1 valine; the molar ratio of aspartic acid/valine ranges from 3.6 aspartic acid/1 valine to 1.4 aspartic acid/1 valine; the molar ratio of aspartic acid/valine ranges from 3.6 aspartic acid/1 valine to 1.5 aspartic acid/1 valine; the molar ratio of aspartic acid/valine ranges from 3.6 aspartic acid/1 valine to 1.6 aspartic acid/1 valine; the molar ratio of aspartic acid/valine ranges from 3.6 aspartic acid/1 valine to 1.7 aspartic acid/1 valine; the molar ratio of aspartic acid/valine ranges from 3.6 aspartic acid/1 valine to 1.8 aspartic acid/1 valine; the molar ratio of aspartic acid/valine ranges from 3.5 aspartic acid/1 valine to 1.8 aspartic acid/1 valine; the molar ratio of aspartic acid/valine ranges from 3.2 aspartic acid/1 valine to 1.9 aspartic acid/1 valine; the molar ratio of aspartic acid/valine ranges from 3.2 aspartic acid/1 valine to 2.0 aspartic acid/1 valine; the molar ratio of aspartic acid/valine ranges from 2.5 aspartic acid/1 valine to 2.0 aspartic acid/1 valine; the molar ratio of aspartic acid/valine ranges from 2.2 aspartic acid/1 valine to 2.0 aspartic acid/1 valine; the molar ratio of aspartic acid/valine ranges from 2.1 aspartic acid/1 valine to 2.0 aspartic acid/1 valine; the molar ratio of aspartic acid/valine is about 3.8 aspartic acid/1 valine; the molar ratio of aspartic acid/valine is about 1.4 aspartic acid/1 valine; the molar ratio of aspartic acid/valine is about 3.2 aspartic acid/1 valine; or the molar ratio of aspartic acid/valine is about 2 aspartic acid/1 valine.

Embodiment 43—The formulation according to any one of embodiments 36-42, wherein the molar ratio of aspartic acid/isoleucine ranges from 5.5 aspartic acid/1 isoleucine to 1.5 aspartic acid/1 isoleucine; the molar ratio of aspartic acid/isoleucine ranges from 5.5 aspartic acid/1 isoleucine to 1.6 aspartic acid/1 isoleucine; the molar ratio of aspartic acid/isoleucine ranges from 5.5 aspartic acid/1 isoleucine to 1.7 aspartic acid/1 isoleucine; the molar ratio of aspartic acid/isoleucine ranges from 5.5 aspartic acid/1 isoleucine to 1.8 aspartic acid/1 isoleucine; the molar ratio of aspartic acid/isoleucine ranges from 5.5 aspartic acid/1 isoleucine to 1.9 aspartic acid/1 isoleucine; the molar ratio of aspartic acid/isoleucine ranges from 5.5 aspartic acid/1 isoleucine to 2.0 aspartic acid/1 isoleucine; the molar ratio of aspartic acid/isoleucine ranges from 5.0 aspartic acid/1 isoleucine to 1.5 aspartic acid/1 isoleucine; the molar ratio of aspartic acid/isoleucine ranges from 5.0 aspartic acid/1 isoleucine to 1.6 aspartic acid/1 isoleucine; the molar ratio of aspartic acid/isoleucine ranges from 5.0 aspartic acid/1 isoleucine to 1.7 aspartic acid/1 isoleucine; the molar ratio of aspartic acid/isoleucine ranges from 5.0 aspartic acid/1 isoleucine to 1.8 aspartic acid/1 isoleucine; the molar ratio of aspartic acid/isoleucine ranges from 5.0 aspartic acid/1 isoleucine to 1.9 aspartic acid/1 isoleucine; the molar ratio of aspartic acid/isoleucine ranges from 5.0 aspartic acid/1 isoleucine to 2.0 aspartic acid/1 isoleucine; the molar ratio of aspartic acid/isoleucine ranges from 4.9 aspartic acid/1 isoleucine to 2.5 aspartic acid/1 isoleucine; the molar ratio of aspartic acid/isoleucine ranges from 4.8 aspartic acid/1 isoleucine to 2.5 aspartic acid/1 isoleucine; the molar ratio of aspartic acid/isoleucine ranges from 4.7 aspartic acid/1 isoleucine to 2.5 aspartic acid/1 isoleucine; the molar ratio of aspartic acid/isoleucine ranges from 4.6 aspartic acid/1 isoleucine to 2.5 aspartic acid/1 isoleucine; the molar ratio of aspartic acid/isoleucine ranges from 4.5 aspartic acid/1 isoleucine to 2.5 aspartic acid/1 isoleucine; the molar ratio of aspartic acid/isoleucine ranges from 4.4 aspartic acid/1 isoleucine to 2.5 aspartic acid/1 isoleucine; the molar ratio of aspartic acid/isoleucine ranges from 4.4 aspartic acid/1 isoleucine to 2.6 aspartic acid/1 isoleucine; the molar ratio of aspartic acid/isoleucine ranges from 4.4 aspartic acid/1 isoleucine to 2.7 aspartic acid/1 isoleucine; the molar ratio of aspartic acid/isoleucine ranges from 4.4 aspartic acid/1 isoleucine to 2.8 aspartic acid/1 isoleucine; the molar ratio of aspartic acid/isoleucine is about 5.5 aspartic acid/1 isoleucine; the molar ratio of aspartic acid/isoleucine is about 1.5 aspartic acid/1 isoleucine; the molar ratio of aspartic acid/isoleucine is about 4.4 aspartic acid/1 isoleucine; or the molar ratio of aspartic acid/isoleucine is about 2.8 aspartic acid/1 isoleucine.

Embodiment 44—The formulation according to any one of embodiments 36-43, wherein the molar ratio of aspartic acid/threonine ranges from 5.5 aspartic acid/1 threonine to 1.7 aspartic acid/1 threonine; the molar ratio of aspartic acid/threonine ranges from 5.5 aspartic acid/1 threonine to 1.8 aspartic acid/1 threonine; the molar ratio of aspartic acid/threonine ranges from 5.5 aspartic acid/1 threonine to 1.9 aspartic acid/1 threonine; the molar ratio of aspartic acid/threonine ranges from 5.5 aspartic acid/1 threonine to 2.0 aspartic acid/1 threonine; the molar ratio of aspartic acid/threonine ranges from 5.0 aspartic acid/1 threonine to 1.7 aspartic acid/1 threonine; the molar ratio of aspartic acid/threonine ranges from 5.0 aspartic acid/1 threonine to 1.8 aspartic acid/1 threonine; the molar ratio of aspartic acid/threonine ranges from 5.0 aspartic acid/1 threonine to 1.9 aspartic acid/1 threonine; the molar ratio of aspartic acid/threonine ranges from 5.0 aspartic acid/1 threonine to 2.0 aspartic acid/1 threonine; the molar ratio of aspartic acid/threonine ranges from 4.9 aspartic acid/1 threonine to 2.5 aspartic acid/1 threonine; the molar ratio of aspartic acid/threonine ranges from 4.8 aspartic acid/1 threonine to 2.5 aspartic acid/1 threonine; the molar ratio of aspartic acid/threonine ranges from 4.7 aspartic acid/1 threonine to 2.5 aspartic acid/1 threonine; the molar ratio of aspartic acid/threonine ranges from 4.6 aspartic acid/1 threonine to 2.5 aspartic acid/1 threonine; the molar ratio of aspartic acid/threonine ranges from 4.5 aspartic acid/1 threonine to 2.5 aspartic acid/1 threonine; the molar ratio of aspartic acid/threonine ranges from 4.4 aspartic acid/1 threonine to 2.5 aspartic acid/1 threonine; the molar ratio of aspartic acid/threonine ranges from 4.4 aspartic acid/1 threonine to 2.6 aspartic acid/1 threonine; the molar ratio of aspartic acid/threonine ranges from 4.4 aspartic acid/1 threonine to 2.7 aspartic acid/1 threonine; the molar ratio of aspartic acid/threonine ranges from 4.4 aspartic acid/1 threonine to 2.8 aspartic acid/1 threonine; the molar ratio of aspartic acid/threonine is about 5.5 aspartic acid/1 threonine;

the molar ratio of aspartic acid/threonine is about 1.7 aspartic acid/1 threonine; the molar ratio of aspartic acid/threonine is about 4.4 aspartic acid/1 threonine; or the molar ratio of aspartic acid/threonine is about 2.8 aspartic acid/1 threonine.

Embodiment 45—The formulation according to any one of embodiments 36-44, wherein the molar ratio of aspartic acid/tyrosine ranges from 40.0 aspartic acid/1 tyrosine to 9.0 aspartic acid/1 tyrosine; the molar ratio of aspartic acid/tyrosine ranges from 36.0 aspartic acid/1 tyrosine to 10.0 aspartic acid/1 tyrosine; the molar ratio of aspartic acid/tyrosine ranges from 36.0 aspartic acid/1 tyrosine to 15.0 aspartic acid/1 tyrosine; the molar ratio of aspartic acid/tyrosine ranges from 36.0 aspartic acid/1 tyrosine to 20.0 aspartic acid/1 tyrosine; the molar ratio of aspartic acid/tyrosine ranges from 24.0 aspartic acid/1 tyrosine to 10.0 aspartic acid/1 tyrosine; the molar ratio of aspartic acid/tyrosine ranges from 24.0 aspartic acid/1 tyrosine to 15.0 aspartic acid/1 tyrosine; the molar ratio of aspartic acid/tyrosine ranges from 24.0 aspartic acid/1 tyrosine to 20.0 aspartic acid/1 tyrosine; the molar ratio of aspartic acid/tyrosine is about 35.8 aspartic acid/1 tyrosine; the molar ratio of aspartic acid/tyrosine is about 23.8 aspartic acid/1 tyrosine; the molar ratio of aspartic acid/tyrosine is about 23.0 aspartic acid/1 tyrosine; the molar ratio of aspartic acid/tyrosine is about 17.5 aspartic acid/1 tyrosine; the molar ratio of aspartic acid/tyrosine is about 15.3 aspartic acid/1 tyrosine; or the molar ratio of aspartic acid/tyrosine is about 11.7 aspartic acid/1 tyrosine.

Embodiment 46—The formulation according to any one of embodiments 36-45, wherein a total weight percent of aspartic acid and serine is greater than a total weight percent of valine, isoleucine, threonine, and tyrosine.

Embodiment 47—The formulation according to any one of embodiments 1-46, wherein the formulation further comprises at least one salt.

Embodiment 48—The formulation according to any one of embodiments 1-47, wherein the formulation further comprises a pharmaceutically acceptable carrier, buffer, adjuvant, or excipient.

Embodiment 49—The formulation according to any one of embodiments 1-48, wherein the formulation does not comprise monosaccharide glucose, at least one glucose-containing disaccharide, or any combination thereof; or when present, the total concentration of the monosaccharide glucose, the at least one glucose-containing disaccharide, or any combination thereof is greater than 0 mM and less than 200 mM.

Embodiment 50—The formulation according to embodiment 49, wherein the formulation comprises: monosaccharide glucose, at least one glucose-containing disaccharide, or any combination thereof, wherein the total concentration of the monosaccharide glucose, the at least one glucose-containing disaccharide, or any combination thereof ranges from 0.01 mM to 200 mM; ranges from 0.1 mM to 200 mM; ranges from 0.01 mM to 100 mM; ranges from 0.1 mM to 100 mM; ranges from 1 mM to 100 mM; ranges from 5 mM to 100 mM; ranges from 10 mM to 100 mM; ranges from 25 mM to 100 mM; ranges from 50 mM to 100 mM; ranges from 75 mM to 100 mM; ranges from 0.01 mM to 90 mM; ranges from 0.1 mM to 90 mM; ranges from 1 mM to 90 mM; ranges from 5 mM to 90 mM; ranges from 10 mM to 90 mM; ranges from 25 mM to 90 mM; ranges from 50 mM to 90 mM; or ranges from 75 mM to 90 mM.

Embodiment 51—The formulation according to any one of embodiments 1, 15, 21, 36, or 38, wherein the formulation further comprises water.

Embodiment 52—The formulation according to any one of embodiments 1-51, wherein the formulation is sterile.

Embodiment 53—The formulation according to any one of embodiments 1-52, wherein at least one of the free amino acids or each of the free amino acids is an L-amino acid.

Embodiment 54—The formulation according to any one of embodiments 1-53, wherein the increased rate determined relative to the same formulation without free amino acids comprises a relative increase ranging from 15% to 200%.

Embodiment 55—The formulation according to any one of embodiments 1-54, wherein the formulation does not comprise free amino acids of lysine, glycine, or tryptophan, or any combination thereof; or when present, each of the free amino acids of lysine, glycine, or tryptophan, or any combination thereof is present in a negligible amount.

Embodiment 56—The formulation according to any one of embodiments 1-55, wherein the formulation is formulated for administration by an enteral route.

Embodiment 57—The formulation according to any one of embodiments 1-56, wherein the formulation is formulated for oral administration.

Embodiment 58—The formulation according to any one of embodiments 1-57, wherein the subject is a mammal.

Embodiment 59—The formulation according to any one of embodiments 1-58, wherein the mammal is a human, cat, dog, pig, horse, cow, sheep, or goat.

Embodiment 60—The formulation according to any one of embodiments 1-59, wherein the mammal is a human.

Embodiment 61—The formulation according to any one of embodiments 1-60, wherein the formulation is used to promote hydration in a healthy subject. Such subjects may, for example, be engaged in physical activities that reduce hydration levels. In some embodiments, the human or other mammal is an elderly subject (e.g., a human equal to or over the age of 70 years). In some embodiments, an elderly subject may exhibit decreased fluid intake relative to a recommended intake suggested by a medical practitioner attending to the elderly subject or standards set by the medical establishment.

Embodiment 62—The formulation according to any one of embodiments 1-60, wherein the formulation is used for the treatment of a disease or disorder associated with dehydration in a subject in need thereof. Exemplary such diseases or disorders associated with dehydration comprise: a fever; edema, which results in increased loss of fluids into abdominal cavities or organs (such as that observed with, for example, peritonitis); incontinence (particularly in humans equal to or over the age of 70 years), which results in increased loss of fluids via increased urine production; and/or renal failure.

Embodiment 63—The formulation according to any one of embodiments 1-60, wherein the formulation is used in the preparation of a medicament for treating a disease or disorder associated with dehydration in a subject in need thereof. Exemplary such diseases or disorders associated with dehydration comprise: a fever; edema, which results in increased loss of fluids into abdominal cavities Of organs (such as that observed with, for example, peritonitis); incontinence (particularly in humans equal to or over the age of 70 years), which results in increased loss of fluids via increased urine production; and/or renal failure.

Embodiment 64—The formulation according to any one of embodiments 1-60, wherein the formulation is used in a method for treating a disease or disorder associated with dehydration in a subject in need thereof. Exemplary such diseases or disorders associated with dehydration comprise: a fever; edema, which results in increased loss of fluids into abdominal cavities or organs (such as that observed with, for example, peritonitis); incontinence (particularly in humans equal to or over the age of 70 years), which results in increased loss of fluids via increased urine production; and/or renal failure.

In any one of embodiments 1-64, a concentration of each of the free amino acids present in the formulation ranges from 0.1 mM to 30 mM. In some embodiments, a concentration of each of free amino acids of aspartic acid, serine, valine, isoleucine, and threonine present in the formulation ranges from 5 mM to 30 mM. In some embodiments, a concentration of each of free amino acids of aspartic acid, serine, and valine present in the formulation ranges from 8 mM to 30 mM. In some embodiments, a concentration of each of free amino acids of aspartic acid and serine present in the formulation ranges from 10 mM to 30 mM. In some embodiments, the pH ranges from 2.0 to 8.0, 2.5 to 8.0, 3.0 to 8.0, 3.5 to 8.0, 4.0 to 8.0, 4.5 to 8.0, 5.0 to 8.0, 5.5 to 8.0, 6.0 to 8.0, 6.5 to 8.0, 7.0 to 8.0, 7.5 to 8.0, 2.0 to 3.0, 2.5 to 4.0; 3.0 to 4.0; 3.3 to 3.8, or is about 2.5, 2.6, 2.9, 3.4, or 3.8.

Variations, modifications and alterations to embodiments of the present disclosure described above will make themselves apparent to those skilled in the art. All such variations, modifications, alterations and the like are intended to fall within the spirit and scope of the present disclosure, limited solely by the appended claims.

While several embodiments of the present disclosure have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

Any feature or element that is positively identified in this description may also be specifically excluded as a feature or element of some embodiments of the present as defined in the claims.

The disclosure described herein may be practiced in the absence of any element or elements, limitation or limitations, which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure.

EXAMPLES

Example 1

Single-pass intestinal perfusion assay in rats: Since 80% of electrolyte and fluid absorption occurs in the small intestine, a small intestine model was used to examine absorption rate of formulations described herein.
Methods
Sprague Dawley (outbred strain), male rats (10-12 weeks old, approx. 350-450 g) were fasted for 16 hours prior surgery (there was no difference in absorption rates between fasted and non-fasted rats). General inhalation anesthesia was induced with 4% isoflurane and further maintained with 2% isoflurane in 2 L/min oxygen. Body temperature was controlled throughout the experiment by placing the rat on a heating pad, and if necessary additional heat was applied using a heating lamp. The ventral abdomen was aseptically prepared (clipped and disinfected) and surgically opened at the midline/linea alba, an approximately 3-5 cm long segment of ileum and distal jejunum was exteriorized, and the distal and proximal ends of the segment were ligated with 2-0 silk while maintaining a continuous blood supply to the intestinal segment. A sterile 5Fr, 15" feeding tube was placed into the lumen of the proximal end through an incision at the antimesenteric side, and a sterile medical grade silicone tube (2 mm ID) was placed at the antimesenteric side into the distal lumen of the emptied intestinal segment, and both tubings were secured with silk ligatures. The intestinal segment with the tubings attached was moved back into the abdomen, and the abdominal wall was closed with 3-0 Nylon sutures and covered with paper towels serving as "blankets". The feeding tube was connected to the perfusion pump, and the intestinal segment was perfused with the test formulation at a perfusion rate of 150 μL/min. Perfusate was collected every 15 minutes from the distal tubing as follows: in the range of 0-90 min: Balancing and early absorption rates (6 samples) and in the range of 90-180 min: Late absorption rates (6 samples). The rectal temperature was monitored every 15 minutes throughout the experiment, and the heating sources were adjusted to assure a physiological body temperature of at least 97° F. was maintained throughout the experiment. After the last sampling, heart blood and intestinal tissues were collected for further analyses. The length of the intestinal segment and the perfusate volume were measured, and the absorption rate (μL/min/cm$^2$) was calculated based on the perfused area and the perfusion rate.
Results
At 15-90 minutes of perfusion with the indicated test formulation, the absorption rate was determined. As shown in FIG. 1, the absorption rate of 6AA-Hyd (6 amino acid combination: aspartic acid, serine, valine, threonine, isoleucine, and tyrosine in in Control solution of Ringer's saline with 17 mM Na) was about 2.3 times (about 131%) more than that of the Control solution [Control (Ringer's saline with 17 mM Na)]. The difference in absorption rate between 6AA-Hyd and Control was statistically significant as reflected by, for example, the error bars presented in FIG. 1.

A significant differential between 6AA-Hyd and Control persisted even at later assay times. At 105-180 minutes of perfusion with the indicated test formulation, for example, the absorption rate of 6AA-Hyd was about 1.8 times (about 83%) more than that of the control solution [Control (Ringer's saline with 17 mM Na)]. See FIG. 2. The difference in absorption rate between 6AA-Hyd and Control was statistically significant as reflected by, for example, the error bars presented in FIG. 2.

For the purposes of comparison, the absorption rate following 15-90 minutes of perfusion or 105-180 minutes of perfusion was determined for 6AA-Hyd (6 amino acid combination: aspartic acid, serine, valine, threonine, isoleucine, and tyrosine in control solution) and compared to 8AA [an amino acid formulation comprising 8 amino acids (aspartic acid, serine, valine, threonine, isoleucine, tyrosine, lysine, and glycine) in control solution] and Control (Ringer's saline with 17 mM Na). As shown in FIG. 3A, 6AA-Hyd exhibited an absorption rate that was about 1.7 times (about 74%) more than that of 8AA and exhibited an absorption rate that was about 1.9 times (about 87%) more than that of Control (Ringer's saline with 17 mM Na) following 15-90 minutes of perfusion. As shown in FIG. 3B, 6AA-Hyd exhibited an absorption rate that was about 1.4 times (about 39%) more than that of 8AA and exhibited an absorption rate that was about 1.7 times (about 72%) more than that of Control (Ringer's saline with 17 mM Na) following 105-180 minutes of perfusion.

Example 2

Sodium (Na) Absorption Studies: measure net fluid and electrolyte absorption, wherein absorptive processes occur predominantly in the tip of the villi and secretory processes occur in the crypt. Na absorption studies were performed on certain of the amino acids present in 6AA-Hyd. See, for example, FIG. 4. As shown in FIG. 4, aspartic acid, serine, and valine increase net Na absorption relative to a control as determined in an Ussing chamber, which method is detailed herein below.
Methods
Ussing Chamber—Sodium Flux (General)

Small intestinal mucosal tissues (ileum and jejunum) from 8-week old male Swiss mice were mounted in Ussing chambers containing isotonic Ringer solution, that was bubbled with 95% O2 and 5% CO2 and maintained at 37° C. throughout the experiment. After the tissues were allowed to stabilize, the conductance (G; expressed as mS/cm2) was recorded, and intestinal tissues were paired based on similar conductance. Sodium radioisotope (22Na) was added to either the basolateral or apical side of each tissue pair (Hot). Ringer samples were taken every 15 minutes from the contralateral sides (Cold). Sample 22Na activity was analyzed using a gamma counter, and unidirectional net sodium flux (Jnet; μeq·cm2·h−1) was calculated.

$$Jnet = \frac{(\text{Cold } CPM2 - \text{Blank}) - [(\text{Cold } CPM1 - \text{Blank}) \times 9/10] \times 5 \times 4 \times 140}{(\text{Hot } CPM - \text{Blank}) \times 10 \times 0.3}$$

[CPM=count per minute, CPM1=previous sample, CPM2=following sample; Blank=no 22Na added; 9/10=dilution factor for each sample (0.5 mL to 5 mL); 5=chamber volume (5 mL); 4=time factor (15 min to 60 min); 140=sodium concentration; Hot CPM="Hot" sample activity; Cold CPM="Cold" sample activity; 10=volume factor for Hot sample (0.1 mL to 1 mL); 0.3=intestinal surface area (cm2)]

As shown in FIG. 4, net sodium absorption conferred by each of free amino acids of aspartic acid, serine, and valine in solution is significantly higher than that of control solution. Increased net sodium absorption is associated with increased net water absorption where water diffuses through the intercellular space into the circulation in response to the osmotic sodium gradient established by, for example, the sodium-hydrogen exchanger 3 (NHE3) or amino acid cotransport. Increased sodium absorption is associated with increased NHE3 expression at the apical membrane and sodium-coupled amino acid transport.

Example 3

Purpose: To test the influence of a beverage comprising 6AA-Hyd on the plasma intestinal fatty acid binding protein (IFABP) response to exercise-heat stress.

Brief Background: Exercise-induced gut damage and intestinal permeability are recognized phenomena that are exacerbated by environmental heat stress and physiological heat strain. Two natural consequences of exercise-heat stress include a reduction in splanchnic blood flow and an increase in body heat storage, both of which are related to the intensity and duration of exercise as well as any environmental limits placed on biophysical heat exchange. Both splanchnic hypoperfusion and hyperthermia increase markers of intestinal epithelial damage (e.g., IFABP) and intestinal epithelial permeability (e.g., lactulose-mannitol ratio, L:M). Indirect measurements of gut damage and permeability are consistent with direct measurements of disrupted intestinal tight junction proteins. Reduced cellular oxygen tension, increased cellular temperature, cytokine-mediated inflammation, or some combination of these effects are thought to contribute to gut damage and permeability. Approaches aimed at protecting the gut (e.g., reducing IFABP in the blood) and perhaps mitigating the most severe intestinal consequences of exercise-heat stress remain limited.

Barrier function is associated at least in part with tight junction integrity. Improvement in tight junction integrity is associated with reduced measurements of intestinal permeability, decreases in transmembrane claudin-2 protein expression, and increases in occludin and e-cadherin proteins. Barrier restoration of damaged epithelia of the unrestricted flux pathway is also demonstrable by improvements in crypt and villus morphology and LGR5+ stem cell proliferation. Improved barrier function reduces gut endotoxin leakage and systemic inflammation.

Design:
One group of volunteers (e.g., 5 volunteers) will drink two bottles (474 mL) of beverage comprising 6AA-Hyd daily for one week. Volunteers will then run on a treadmill (TM) at 60% of maximal oxygen uptake for 2-hours in a 35° C. environmental chamber. Blood samples will be taken immediately before exercise, immediately after exercise, and again 1 and 2 hours post exercise. Volunteers will drink one bottle (237 mL) of the beverage comprising 6AA-Hyd immediately before exercise and every 20 minutes during the 2-hour exercise bout (7 bottles in total, 1.659 L). After exercise water will be permitted ad libitum. Blood will be sampled for IFABP.

Analysis:
The individual (e.g., n=5) changes in IFABP (ΔIFABP) from pre- to post exercise will be compared to the ΔIFABP 95% confidence interval observed for both sports drink trials and control trials (water) using a research database. Data falling within the water interval will be considered negative outcomes. Data falling outside the water interval will be considered positive outcomes. Data falling between each interval will be considered inconclusive.

What is claimed is:

1. A formulation, wherein the formulation consists of:
a therapeutically effective combination of free amino acids consisting of tyrosine, isoleucine, threonine, valine, serine, and aspartic acid;
wherein the molar ratio of aspartic acid/serine ranges from 2.8 aspartic acid/1 serine to 1 aspartic acid/1 serine;
wherein the molar ratio of aspartic acid/valine ranges from 3.8 aspartic acid/1 valine to 1.4 aspartic acid/1 valine;
wherein the molar ratio of aspartic acid/isoleucine ranges from 5.5 aspartic acid/1 isoleucine to 1.5 aspartic acid/1 isoleucine;
wherein the molar ratio of aspartic acid/threonine ranges from 5.5 aspartic acid/1 threonine to 1.3 aspartic acid/1 threonine;
wherein the molar ratio of aspartic acid/tyrosine ranges from 40.0 aspartic acid/1 tyrosine to 9.0 aspartic acid/1 tyrosine;
and
at least one pharmaceutically acceptable electrolyte, wherein the electrolyte comprises 17 mM-140 mM sodium;
optionally, at least one pharmaceutically acceptable carrier, buffer, adjuvant, excipient, or water, or any combination thereof.

2. The formulation according to claim 1, wherein a total weight percent of aspartic acid and serine is greater than a total weight percent of valine, isoleucine, threonine, and tyrosine.

3. The formulation according to claim 1, wherein each of the free amino acids has a concentration ranging from 0.1 mM-30 mM.

4. The formulation according to claim 3, wherein the formulation is for use in promoting hydration or intestinal barrier function in a subject in need thereof.

5. The formulation according to claim 4, wherein the therapeutically effective combination of free amino acids is sufficient to promote fluid absorption or intestinal barrier integrity, thereby promoting hydration or intestinal barrier function in the subject.

6. The formulation according to claim 5, wherein the promoted fluid absorption reflects an increased rate of fluid absorption in the subject, wherein the increased rate is determined relative to the same formulation without free amino acids.

7. The formulation according to claim 6, wherein the increased rate determined relative to the same formulation without free amino acids comprises a relative increase of at least 15%.

8. The formulation according to claim 5, wherein the promoted intestinal barrier integrity reflects at least one of a reduction in intestinal permeability; an increase in E-cadherin expression and/or activity; an increase in occludin protein expression and/or activity; a decrease in claudin-2 protein expression and/or function; or any combination thereof.

9. The formulation according to claim 1, wherein a concentration of aspartic acid ranges from 0.1 mM-5 mM.

10. The formulation according to claim 1, wherein at least one of the free amino acids or each of the free amino acids is an L-amino acid.

11. The formulation according to claim 1, wherein the formulation is formulated for administration by an enteral route.

12. The formulation according to claim 11, wherein the formulation is formulated for administration by an oral route.

13. The formulation according to claim 1, wherein a total weight percent of free amino acids of aspartic acid ranges from 30% to 55% of a total weight of the therapeutically effective combination of free amino acids.

* * * * *